(12) United States Patent
Billen et al.

(10) Patent No.: US 8,461,312 B2
(45) Date of Patent: Jun. 11, 2013

(54) METHOD FOR THE PRODUCTION OF 1,4-BENZOTHIEPIN-1,1-DIOXIDE DERIVATIVES

(75) Inventors: Guenter Billen, Frankfurt am Main (DE); Wendelin Frick, Frankfurt am Main (DE); John Patrick Larkin, Market Harborough (GB); Guy Lemaitre, Othis (FR); Francoise Bendetti, Paris (FR); Philippe Boffelli, Paris (FR); Jean-Yves Godard, Paris (FR); Christian Masson, Paris (FR); Veronique Crocq, Paris (FR); Sylvaine Lafont, Paris (FR); Jos Hulshof, Groningen (NL)

(73) Assignee: Sanofi, Paris (FR)

( * ) Notice: Subject to any disclaimer, the term of this patent is extended or adjusted under 35 U.S.C. 154(b) by 165 days.

(21) Appl. No.: 12/990,713

(22) PCT Filed: Apr. 29, 2009

(86) PCT No.: PCT/EP2009/003102
§ 371 (c)(1),
(2), (4) Date: Jun. 16, 2011

(87) PCT Pub. No.: WO2009/132832
PCT Pub. Date: Nov. 5, 2009

(65) Prior Publication Data
US 2011/0245486 A1  Oct. 6, 2011

(30) Foreign Application Priority Data

| May 2, 2008 | (DE) | 10 2008 022 017 |
| Feb. 7, 2009 | (DE) | 10 2009 007 825 |
| Mar. 24, 2009 | (DE) | 10 2009 014 637 |

(51) Int. Cl.
  *C07G 3/00* (2006.01)
  *C07H 17/00* (2006.01)
  *C07H 5/06* (2006.01)
  *C07D 337/00* (2006.01)

(52) U.S. Cl.
  USPC .......................... 536/18.5; 536/29.1; 549/9

(58) Field of Classification Search
  None
  See application file for complete search history.

(56) References Cited

U.S. PATENT DOCUMENTS 5,994,391 A    11/1999  Lee et al.
2004/0147774 A1   7/2004  Crocq-Stuerga et al.

*Primary Examiner* — Layla Bland
(74) *Attorney, Agent, or Firm* — Scully, Scott, Murphy & Presser, P.C.

(57) ABSTRACT

The invention relates to a method for producing 1,4-benzothiepin-1,1-dioxide derivatives substituted with benzyl groups.

12 Claims, No Drawings

METHOD FOR THE PRODUCTION OF 1,4-BENZOTHIEPIN-1,1-DIOXIDE DERIVATIVES

The invention relates to a method for the production of 1,4-benzothiepin 1,1-dioxide derivatives substituted with benzyl radicals.

1,4-Benzothiepin 1,1-dioxide derivatives have already been described (U.S. Pat. No. 5,994,391). However, the method described in U.S. Pat. No. 5,994,391 leads to racemates. The synthesis of the optically pure compounds (intermediate products or end products) requires complex chromatographic purification steps. See, for example, position 3 of compound I from U.S. Pat. No. 5,994,391 or else the intermediate products LI or XLI from U.S. Pat. No. 5,994,391.

The object of the invention was to provide an improved method for the production of certain enantiomerically pure 1,4-benzothiepin 1,1-dioxide derivatives. In particular, the stereo centers at position 3, 4 and 5 of the thiepin system of the compound of the formula I should be built up and/or obtained in optically pure form.

The invention therefore relates to an improved method for the production of the compounds of the formula I

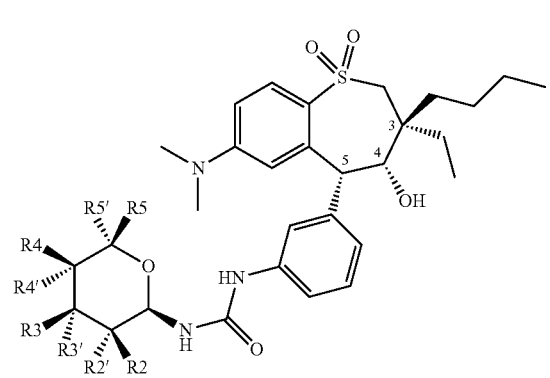

I in which
R2, R2', R3, R3', R4, R4', R5, R5', independently of one another, are H, Cl, Br, I, OH, —(CH$_2$)—OH, CF$_3$, NO$_2$, N$_3$, CN, S(O)$_p$—R6, O—S(O)$_p$—R6, (C$_1$-C$_6$)-alkylene-S(O)$_p$—R6, (C$_1$-C$_6$)-alkylene-O—S(O)$_p$—R6, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, O—(C$_1$-C$_6$)-alkyl, where, in the alkyl radicals, one, more, or all hydrogen(s) can be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

where always at least one of the radicals R2, R2', R3, R3', R4, R4', R5, R5' has the meaning —O—(CH$_2$)$_m$-phenyl or —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

R6 is H, OH, (C$_1$-C$_6$)-alkyl, NH$_2$, NH(C$_1$-C$_6$)-alkyl, N((C$_1$-C$_6$)-alkyl)$_2$;
n is 2, 3, 4, 5, 6;
m is 1, 2, 3, 4, 5, 6;
P is 0, 1, 2;
and pharmaceutically compatible salts thereof.

The invention further relates to improved methods for the production of the compounds of the formulae Ia, Ib and Ic

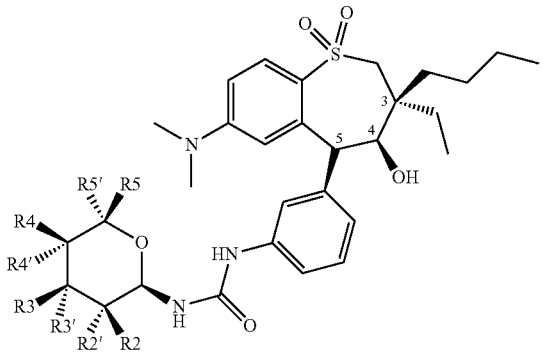

Ia

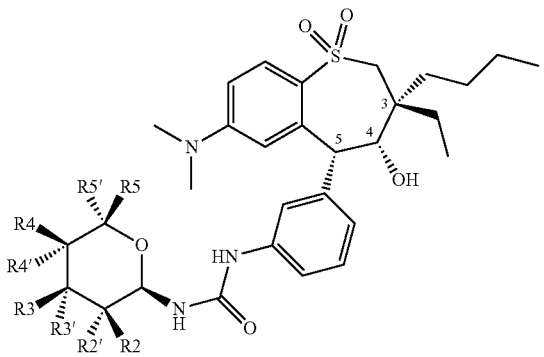

Ib

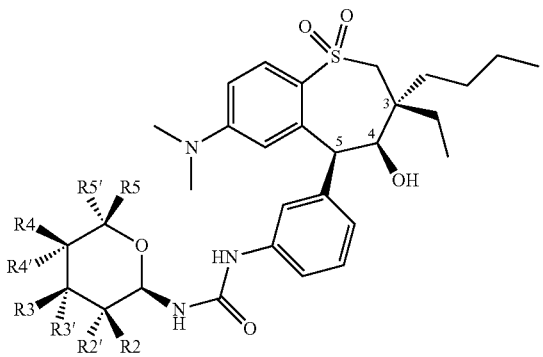

Ic in which
R2, R2', R3, R3', R4, R4', R5, R5', independently of one another, are H, Cl, Br, I, OH, —(CH$_2$)—OH, CF$_3$, NO$_2$, N$_3$, CN, S(O)$_p$—R6, O—S(O)$_p$—R6, (C$_1$-C$_6$)-alkylene-S(O)$_p$—R6, (C$_1$-C$_6$)-alkylene-O—S(O)$_p$—R6, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, O—(C$_1$-C$_6$)-alkyl, where, in the alkyl radicals, one, more, or all hydrogen(s) can be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

where always at least one of the radicals R2, R2', R3, R3', R4, R4', R5, R5' has the meaning —O—(CH$_2$)$_m$-phenyl or —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

R6 is H, OH, (C$_1$-C$_6$)-alkyl, NH$_2$, NH(C$_1$-C$_6$)-alkyl, N((C$_1$-C$_6$)-alkyl)$_2$;

n is 2, 3, 4, 5, 6;

m is 1, 2, 3, 4, 5, 6;

P is 0, 1, 2;

and pharmaceutically compatible salts thereof.

If radicals or substituents can occur several times in the compounds of the formulae I, then they can all, independently of one another, have the stated meaning and be identical or different.

The alkyl, alkenyl, alkynyl, alkylene, alkenylene and alkynylene radicals in the radicals R, R1, R2, R2', R3, R3', R4, R4', R5, R5' and R6 may either be straight-chain or branched. One embodiment of the invention also further relates to individual reaction steps and also intermediate products of this method for the production of the compounds of the formulae 10 and 10a which has the following steps:

The compound of the formula 10 or 10a can be produced, for example, by reacting the compound of the formula 8 with a thiol of the formula 5 or 5a, in the presence of a suitable base, such as, for example, sodium carbonate, potassium carbonate or cesium carbonate, in a suitable solvent, such as, for example, toluene, dimethylformamide, dimethyl sulfoxide or N-methylpyrrolidone.

The reaction temperature here is from 20° C. to 120° C., preferably from 40° C. to 80° C.

The reaction time is generally 0.5 to 8 hours, depending on the composition of the mixture and the selected temperature range.

The resulting compound of the formula 10 or 10a is then separated off from the reaction mixture by aqueous work-up and extraction with a suitable solvent, for example toluene, ethyl acetate or dichloromethane.

The asterisk on one carbon atom in the compound of the formula 10/10a means that the carbon atom in each case is chiral and the compound is present either as R- or S-enantiomer or as a mixture of the two enantiomers.

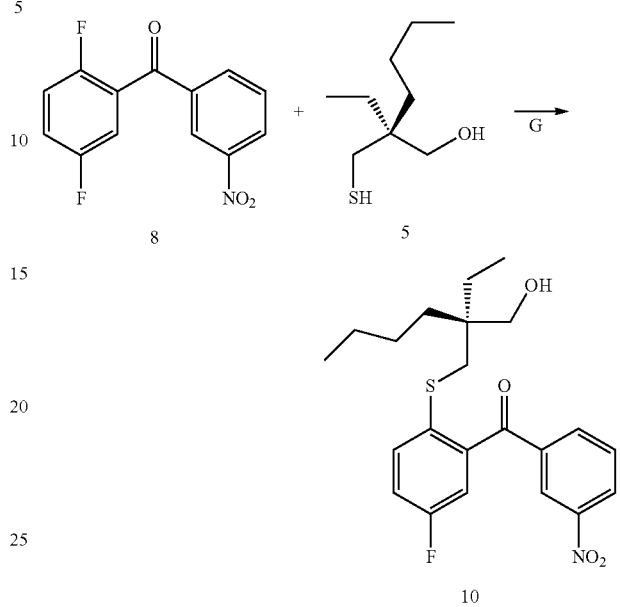

Preferably, the compound 10 or 10a is produced in enantiomerically pure form, for example by reacting the compound of the formula 8 with the compound of the formula 5 under the stated reaction conditions. The compound of the formula 10a is produced analogously by reaction with the compound of the formula 5a.

The compound of the formula 8 can be produced, for example, by reacting the compound of the formula 7 with 3-nitrobenzoyl chloride, in the presence of a suitable catalyst, for example aluminum(III) chloride.

The reaction temperature here is from 40° C. to 140° C., preferably from 80° C. to 120° C. The reaction time is generally 2 to 24 hours, depending on the composition of the mixture and the selected temperature range.

The resulting compound of the formula 8 is then separated off from the reaction mixture by aqueous work-up and extraction in a suitable solvent, for example ethyl acetate or dichloromethane, and subsequent crystallization.

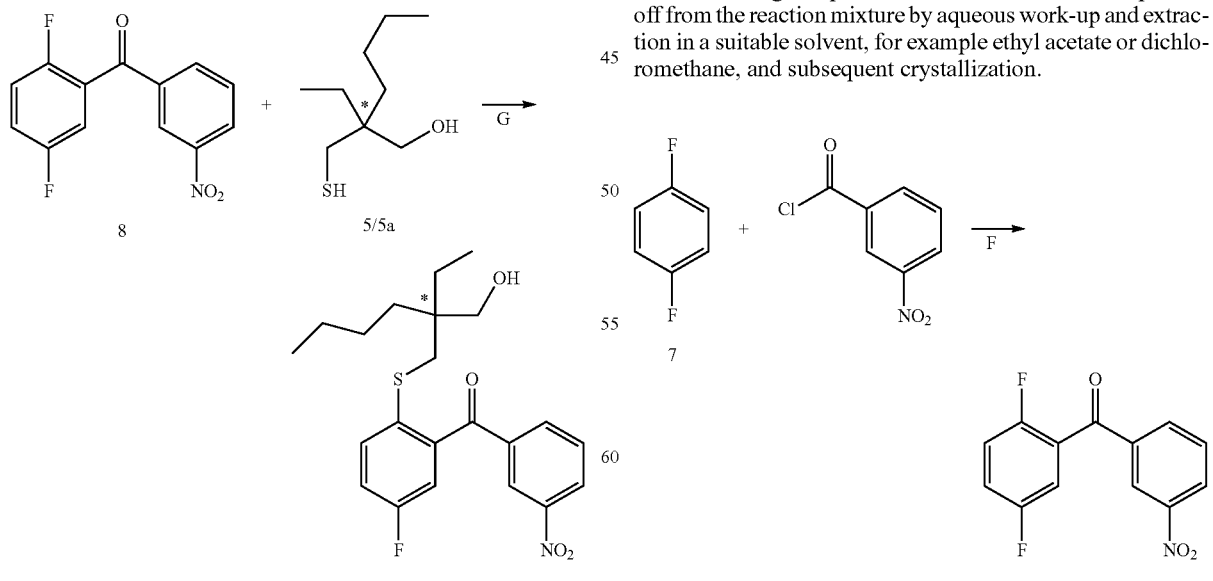

The compound of the formula 1 can be produced, for example, by reacting 2-butyl-2-ethyl-1,3-propanediol with suitable oxidizing agents, for example potassium permanganate. The reaction temperature here is from 0° C. to 100° C., preferably from 0° C. to 40° C. The reaction time is generally 2 to 8 hours, depending on the composition of the mixture and the selected temperature range. The resulting compound of the formula 1 is then separated off from the reaction mixture by aqueous work-up and extraction with a suitable solvent, for example ethyl acetate or dichloromethane. A purification can be carried out with the help of a vacuum distillation.

Furthermore, the compound of the formula 1 can be obtained by methods known in the literature.

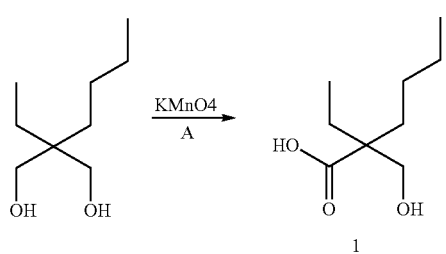

Boehm, Andreas; Petersen, Hermann; Stohrer, Juergen. Regioselective hydroxymethylation process for the preparation of α,α-dialkyl-α-hydroxymethylcarboxylic acid derivatives. EP 1,666,447 A1

Nishii, Sadao. Preparation of 2-ethyl-2-(hydroxymethyl) hexanoic acid. Jpn. Kokai Tokkyo Koho (1989), JP 01139544

The compound of the formula 2a can be produced, for example, by reacting racemic 2-butyl-2-ethyl-1,3-propanediol with chiral bases, for example quinine, in a suitable solvent or solvent mixture, for example toluene, n-butyl acetate or acetone/water. The reaction temperature of the racemate resolution here is 0° C. to 100° C., preferably from 20° C. to 60° C. The reaction time is generally 2 to 24 hours, depending on the composition of the mixture and the selected temperature range. The achieved enantiomer excesses (ee) are between 20 and 80% ee depending on the selected conditions. Higher ee values can be achieved if the resulting compound of the formula 2a is then recrystallized in a suitable solvent or solvent mixture, for example toluene, n-butyl acetate/heptane or acetone/water. The achieved enantiomer excesses (ee) are between 80 and 99% ee depending on the selected conditions.

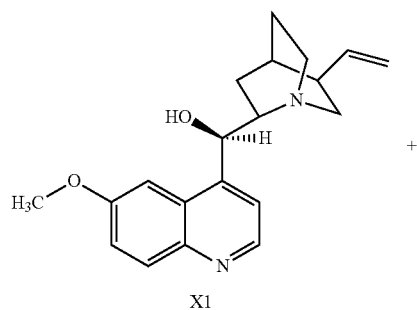

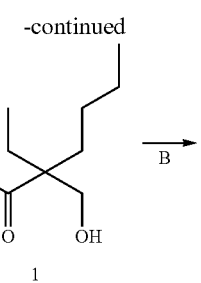

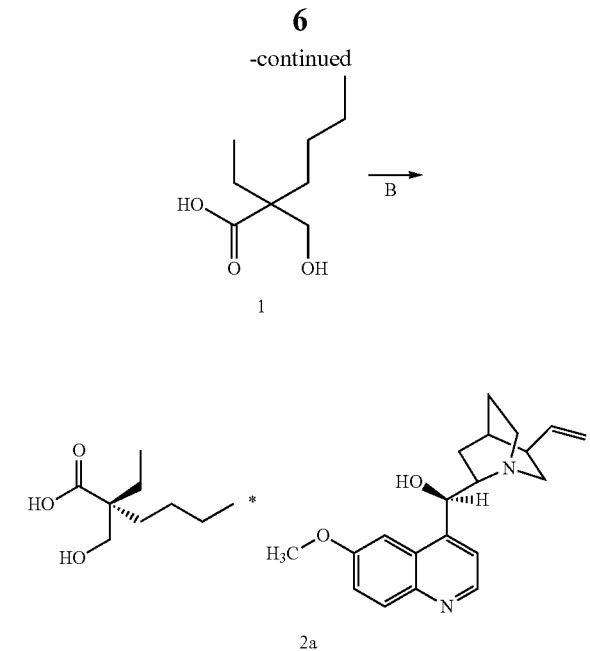

The compound of the formula 2 is then obtained from the compound of the formula 2a by aqueous work-up and extraction with a suitable solvent, for example toluene, ethyl acetate or dichloromethane.

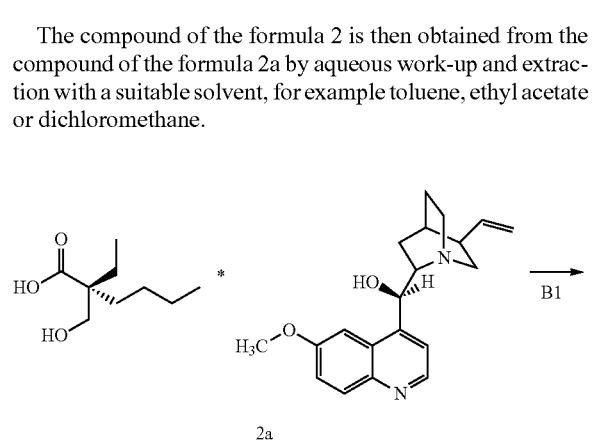

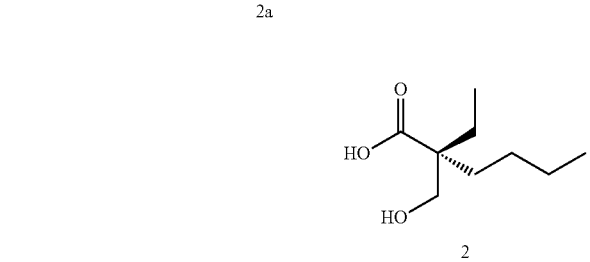

Alternatively, the compound 2 can be produced by racemate resolution with the compound of the formula X2. The compound of the formula 2 is then obtained from the compound of the formula 2b by aqueous work-up and extraction with a suitable solvent, for example toluene, ethyl acetate or dichloromethane.

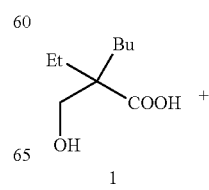

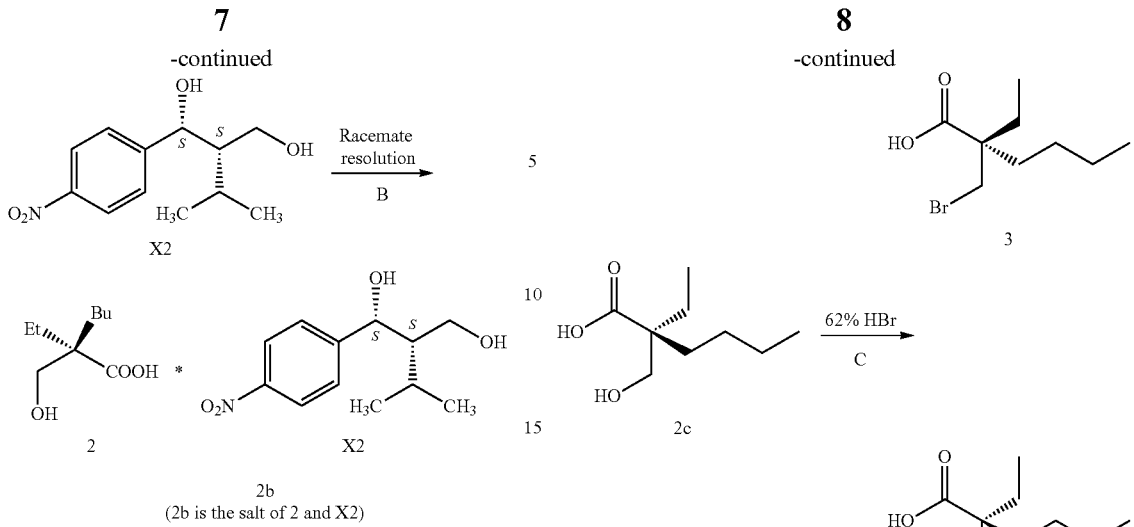

2b
(2b is the salt of 2 and X2)

The enantiomer (formula 2c) of the compound 2 can be produced by racemate resolution with the antipode (formula X3) of the compound X2.

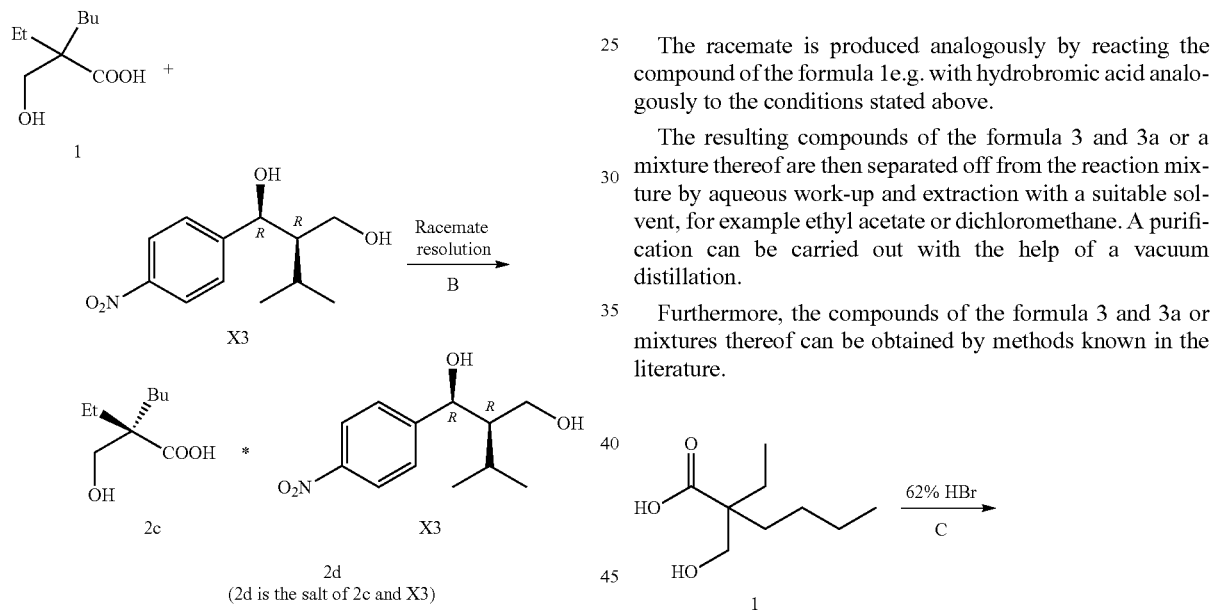

2d
(2d is the salt of 2c and X3)

The compounds of the formula 3 and 3a can be produced for example by reacting the compound of the formula 2 or 2c e.g. with hydrobromic acid with or without a suitable solvent or solvent mixture, for example toluene. The reaction temperature here is 40° C. to 120° C., preferably from 60° C. to 100° C. The reaction time is generally 2 to 24 hours, depending on the composition of the mixture and the selected temperature range. The yields achieved are between 60 and 90% depending on the selected conditions.

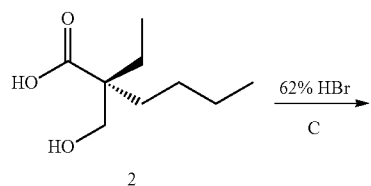

The racemate is produced analogously by reacting the compound of the formula 1 e.g. with hydrobromic acid analogously to the conditions stated above.

The resulting compounds of the formula 3 and 3a or a mixture thereof are then separated off from the reaction mixture by aqueous work-up and extraction with a suitable solvent, for example ethyl acetate or dichloromethane. A purification can be carried out with the help of a vacuum distillation.

Furthermore, the compounds of the formula 3 and 3a or mixtures thereof can be obtained by methods known in the literature.

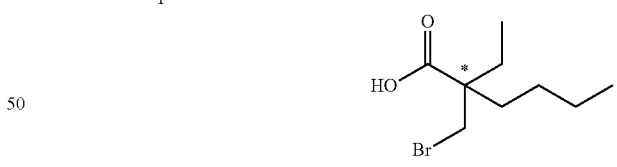

Mitsuda, Masaru; Oguro, Kazumi; Watabe, Kazuhiko; Hayano, Tetsuji. Preparation of 2-substituted-2-(hydroxymethyl)carboxylic acids (esters) and their intermediates.; Jpn. Kokai Tokkyo Koho (2006), JP 2006219404

Crocq, Veronique; Roussel, Patrick. Process for preparation of new chiral compounds derived from esters of hexanoic acid, and their use in the synthesis of the chiral 2-(bromomethyl)-2-ethylhexanoic acid.; FR 2849024

Alternatively, the compound of the formula 3 or 3a can be obtained directly from the salts, e.g. 2a, 2b and 2d, analogously to the described conditions.

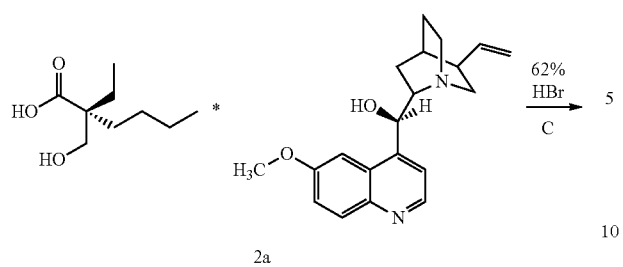

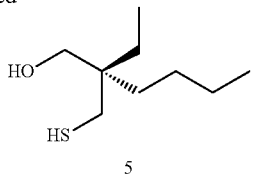

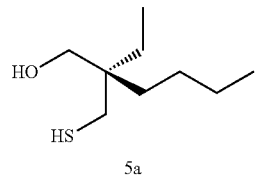

The compound of the formula 5a is synthesized analogously.

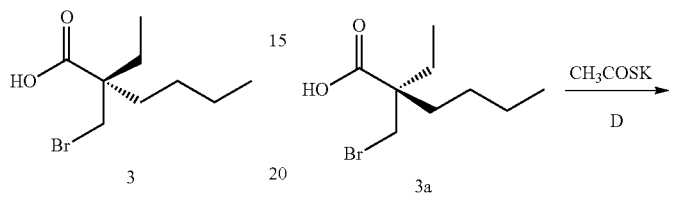

The compound of the formula 5 can be produced, for example, by reacting the bromide of the compound of the formula 3 e.g. with potassium thioacetate in a suitable solvent or solvent mixture, for example toluene or acetone. The reaction temperature here is 0° C. to 100° C., preferably from 20° C. to 40° C. The reaction time is generally 2 to 24 hours, depending on the composition of the mixture and the selected temperature range. The resulting compounds of the formula 4 are then separated off from the reaction mixture by aqueous work-up and extraction with a suitable solvent, for example ethyl acetate or dichloromethane. Preferably, the reaction product is not isolated, but reduced directly in a suitable solvent or solvent mixture, such as e.g. THF/toluene, using a reducing agent such as e.g. lithium aluminum hydride (LAH) to give the compound of the formula 5. The reaction temperature here is 0° C. to 100° C., preferably 0° C. to 40° C. Following aqueous work-up and extraction with a suitable solvent, for example ethyl acetate, toluene or dichloromethane, the product is separated off from the reaction mixture. A purification can be carried out with the help of a vacuum distillation.

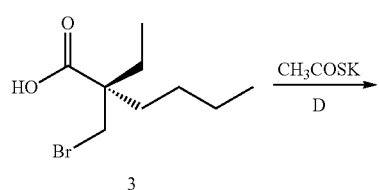

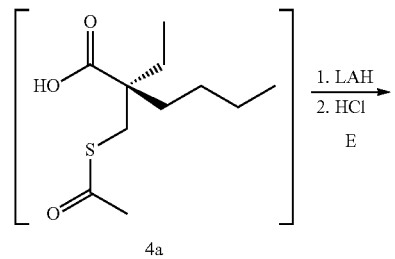

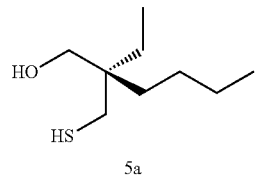

One embodiment of the invention further also relates to individual reaction steps and also intermediate products of this method for the production of the compound of the formula 10 which has the following steps:

The compound of the formula 10 can be produced, for example, by reacting the compound of the formula 8 with a thiol of the formula 35 in the presence of a suitable, aqueous base, such as for example sodium carbonate, potassium carbonate, cesium carbonate.

The reaction temperature here is from 40° C. to 140° C., preferably from 60° C. to 120° C.

The reaction time is generally 3 to 24 hours, depending on the composition of the mixture and the selected temperature range.

The resulting mixture of the compounds of the formula 30/30a and 10/10a is completely converted to the compound of the formula 10/10a by alkaline hydrolysis of the compound of the formula 30/30a, e.g. with sodium methylate in methanol or methanolic potassium hydroxide solution, and is then separated off from the reaction mixture by aqueous work-up and extraction with a suitable solvent, for example toluene, ethyl acetate or dichloromethane.

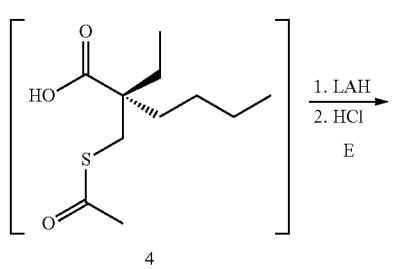

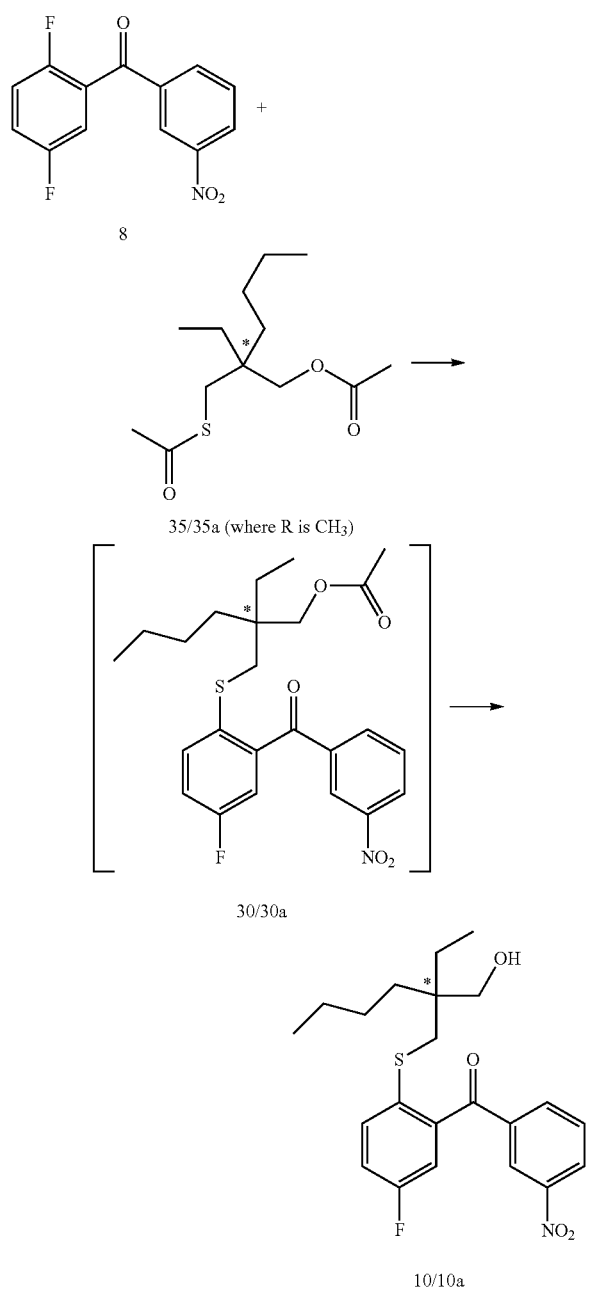
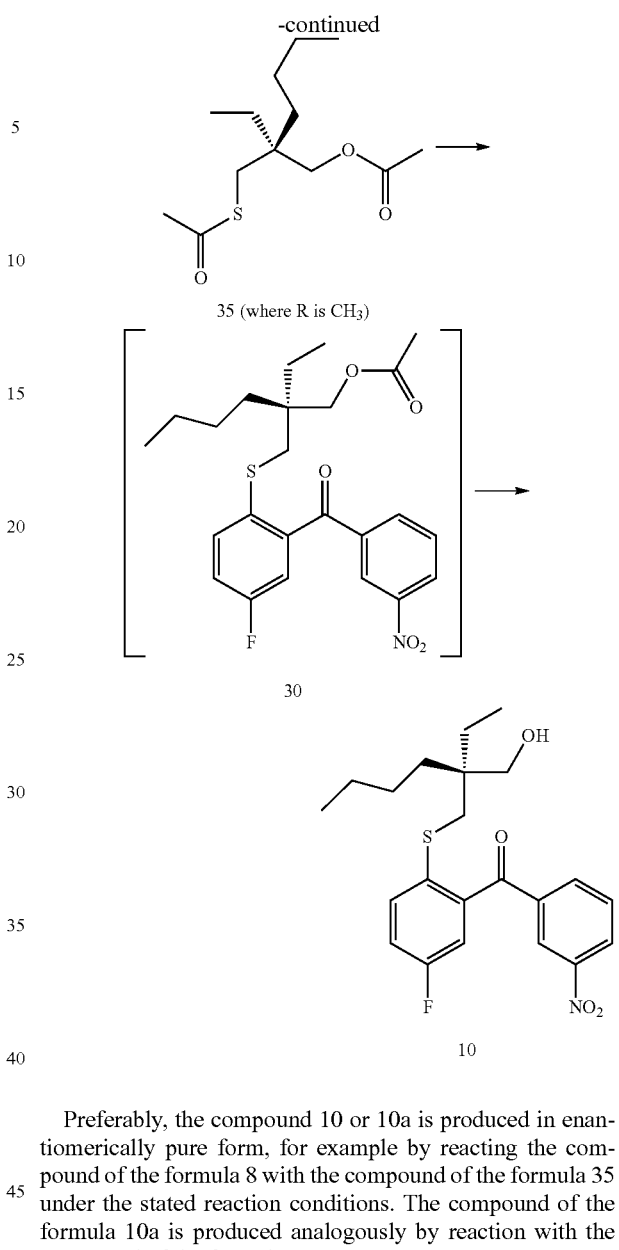

The asterisk on one carbon atom in the compound of the formula 10 means that the carbon atom in each case is chiral and the compound is present either as R- or S-enantiomer or as a mixture of the two enantiomers.

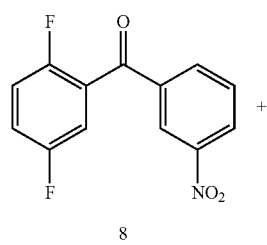

Preferably, the compound 10 or 10a is produced in enantiomerically pure form, for example by reacting the compound of the formula 8 with the compound of the formula 35 under the stated reaction conditions. The compound of the formula 10a is produced analogously by reaction with the compound of the formula 5a.

The compound of the formula 35 can be produced, for example, by reacting the bromide of the compound of the formula 3 e.g. with potassium thioacetate in a suitable solvent or solvent mixture, such as for example toluene or acetone. The reaction temperature here is 0° C. to 100° C., preferably from 20° C. to 40° C. The reaction time is generally 2 to 24 hours, depending on the composition of the mixture and the selected temperature range. The resulting compounds of the formula 4 are then separated off from the reaction mixture by aqueous work-up and extraction with a suitable solvent, for example ethyl acetate or dichloromethane. Preferably, the reaction product is not isolated, but reduced directly to the compound of the formula 5 in a suitable solvent or solvent mixture, such as e.g. THF/toluene, using a reducing agent such as e.g. lithium aluminum hydride. The reaction temperature here is 0° C. to 100° C., preferably 0° C. to 40° C. Following aqueous work-up and extraction with a suitable solvent, for example ethyl acetate, toluene or dichloromethane, the product is reacted with an acid chloride or acid anhydride under conditions known in the literature. Preferably, after reduction has taken place, the reaction mixture is hydrolyzed directly with an acid halide or carboxylic anhydride, such as e.g. acetyl chloride or acetanhydride, and then subjected to aqueous work-up. A purification can be carried out with the help of a vacuum distillation.

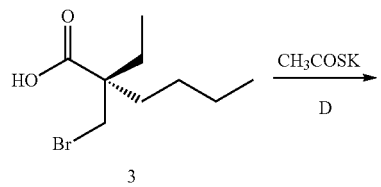

3

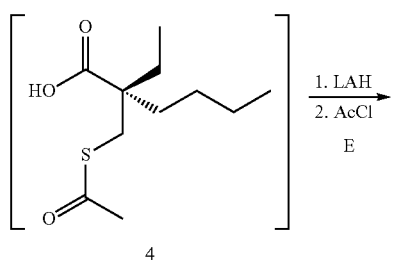

4

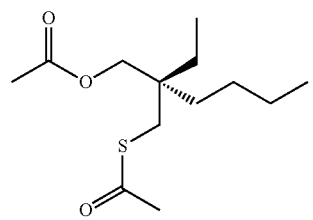

35 (where R is CH₃)

The compound of the formula 35a or of the mixture of 35/35a is produced analogously to the conditions specified for the compound of the formula 35.

One embodiment of the invention further also relates to individual reaction steps and also intermediate products of this method for the production of the compounds of the formula 15, 15a, 15b and 15c which has the following steps:

The compound of the formula 11/11a can be produced, for example, by reacting the compound of the formula 10/10a with a suitable reducing agent, such as for example hydrophosphorous acid/iodine, sodium borohydride/aluminum (III) chloride, triethylsilane/trifluoroacetic acid, isobutylaluminum dichloride, butylsilane/boron trifluoride, polyhydroxymethylsilane (PHMS) or triethylsilane/boron trifluoride without or in a suitable solvent, such as e.g. toluene, THF, methyl-THF or dimethoxyethane. The reaction temperature here is 20° C. to 120° C., preferably from 40° C. to 80° C.

The reaction time is generally 2 to 12 hours, depending on the composition of the mixture and the selected temperature range. The resulting compounds of the formula 11/11a is then separated off from the reaction mixture by aqueous work-up and extraction with a suitable solvent, for example toluene, ethyl acetate, methyl tert-butyl ether or dichloromethane.

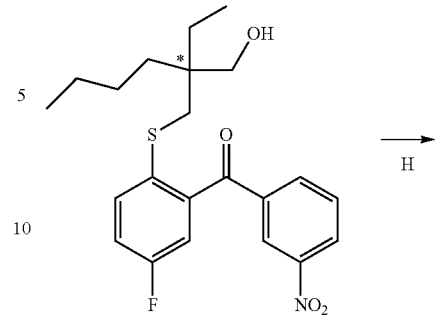

10/10a

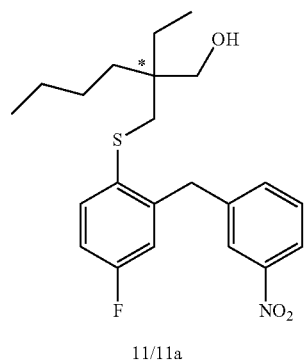

11/11a

The asterisk on one carbon atom in the compounds of the formula 10/10a and 11/11a means that the carbon atom in question is chiral and the compounds are present either as R- or S-enantiomer or as a mixture of the two enantiomers.

The compound of the formula 11 is produced analogously to the conditions specified for the compounds of the formula 11/11a.

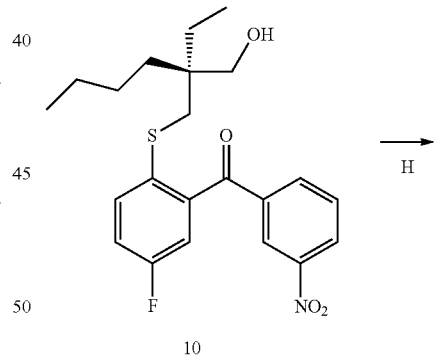

10

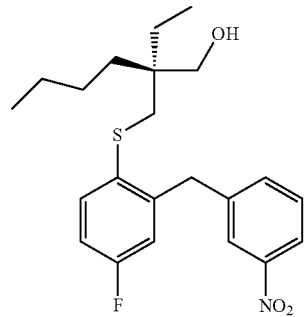

11

The compound of the formula 12 can be produced, for example, by reacting the compound of the formula 11 with a suitable oxidizing agent, such as for example sodium perborate, hydrogen peroxide/sodium tungstate, hydrogen peroxide/molybdenum(IV) oxide dichloride, ozones or hydrogen peroxide/acetonitrile/ethanol in a suitable solvent, such as e.g. toluene, THF, methyl-THF or dimethoxyethane. The reaction temperature here is 0° C. to 120° C., preferably from 20° C. to 80° C.

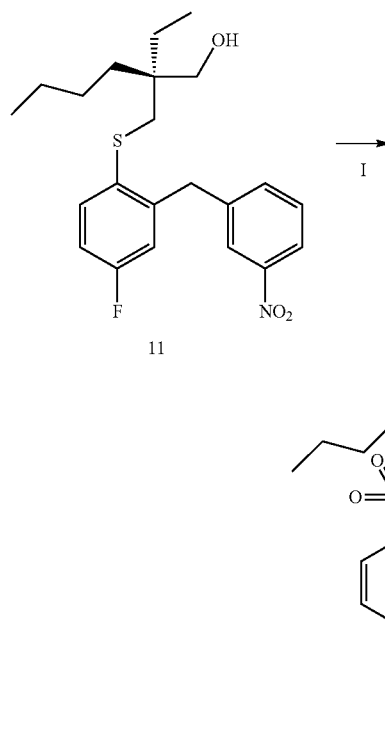

The reaction time is generally 2 to 12 hours, depending on the composition of the mixture and the selected temperature range. The resulting compound of the formula 12 is then separated off from the reaction mixture by aqueous work-up and extraction with a suitable solvent, for example toluene, ethyl acetate, methyl tert-butyl ether or dichloromethane, and crystallized.

The compound of the formula 12a is produced analogously to the conditions specified for the compound of the formula 12.

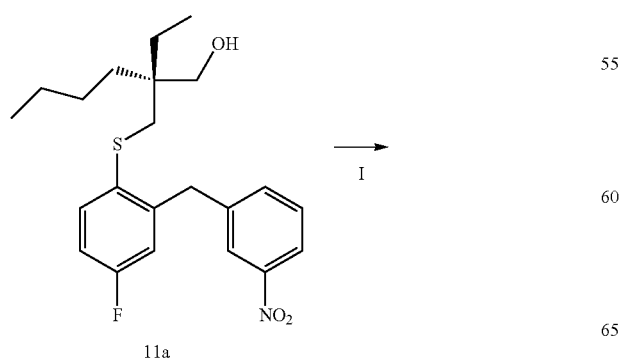

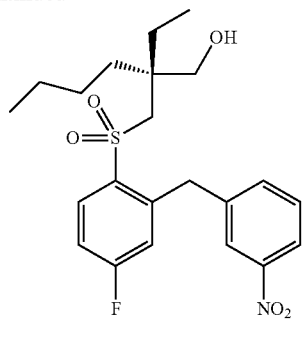

The compound of the formula 13 can be produced, for example, by reacting the compound of the formula 12 with a suitable oxidizing agent, such as for example oxalyl chloride/DMSO, sulfur trioxide-pyridine complex/DMSO, pyridinium dichromate, periodane or sodium hypochloride/TEMPO in the suitable solvent or solvent mixture, such as e.g. toluene, THF, methyl-THF, water or dimethoxyethane. The reaction temperature here is 0° C. to 100° C., preferably from 0° C. to 40° C.

The reaction time is generally 1 to 4 hours, depending on the composition of the mixture and the selected temperature range. The resulting compound of the formula 13 is then separated off from the reaction mixture by aqueous work-up and extraction with a suitable solvent, for example toluene, ethyl acetate, methyl tert-butyl ether or dichloromethane, and crystallized.

The compound of the formula 13a is produced analogously to the conditions specified for the compound of the formula 13.

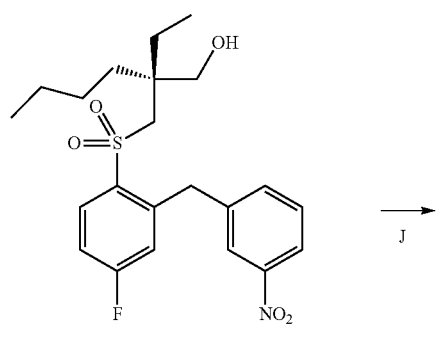

12a

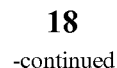

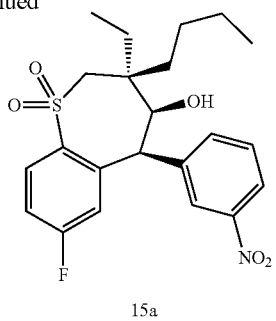

15a

The compounds of the formula 15b and 15c are produced analogously to the conditions specified for the compound of the formula 15 and 15a.

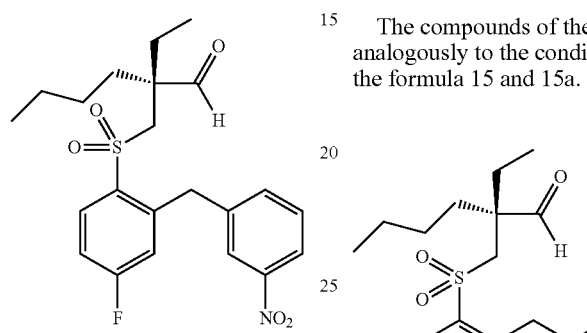

13a

The compound of the formula 15 can be produced, for example, by reacting the compound of the formula 13 with a suitable base, such as for example potassium carbonate, cesium carbonate, DBU, sodium or potassium ethylate or sodium or potassium tert-butylate, a suitable solvent such as e.g. 2-propanol, toluene, THF, methyl-THF or dimethoxyethane. The reaction temperature here is −70° C. to 80° C., preferably from −20° C. to 25° C. The resulting isomer mixture can then be separated by means of chromatographic methods, such as e.g. chromatography on silica gel and toluene/ethyl acetate as mobile phase, or fractional crystallization.

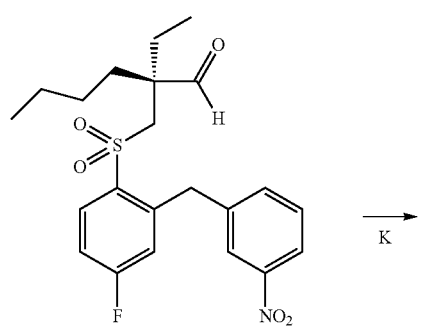

13

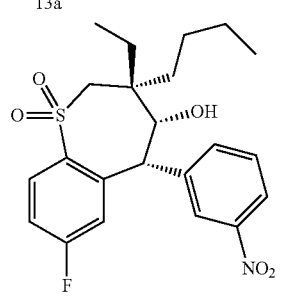

15b

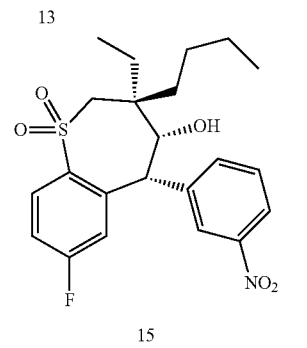

15

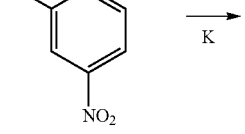

+

15c

One embodiment of the invention further also relates to individual reaction steps and also intermediate products of the method for the production of the compounds of the formulae 17, 17a, 17b and 17c.

The compound of the formula 16 can be produced, for example, by reacting the compound of the formula 15 with a suitable reducing agent, such as for example hydrogen/palladium on activated carbon in a suitable solvent, such as e.g. methanol, ethanol, 2-propanol, dichloromethane, toluene,

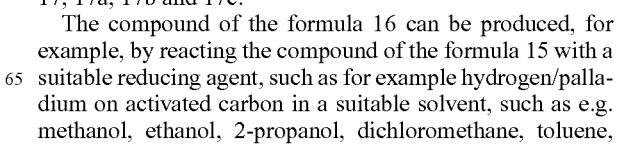

THF, methyl-THF or dimethoxyethane. The reaction temperature here is 0° C. to 80° C., preferably from 20° C. to 50° C.

The reaction time is generally 2 to 12 hours, depending on the composition of the mixture and the selected temperature range.

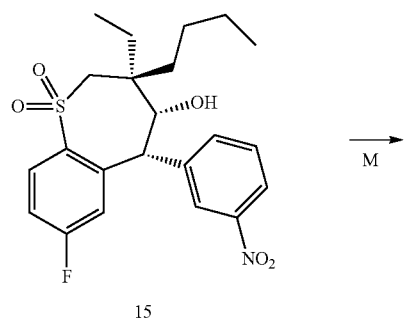

15

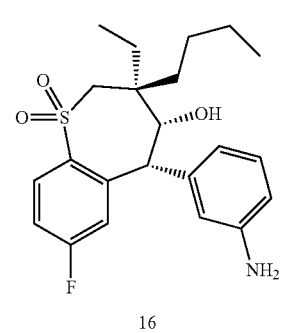

16

The compounds of the formula 16a, 16b and 16c and mixtures thereof are produced analogously to the conditions specified for the compound of the formula 16.

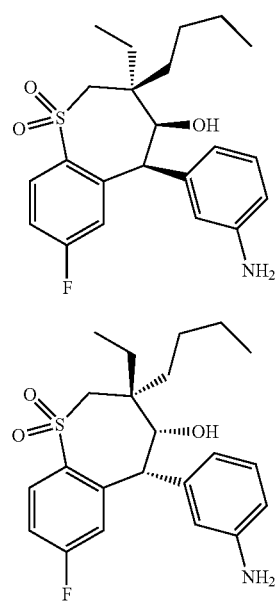

16a

16b

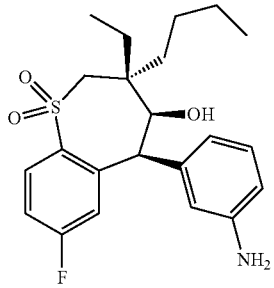

16c

The compound of the formula 17 can be produced, for example, by reacting the compound of the formula 16 with dimethylamine in a suitable solvent, such as e.g. methanol, ethanol, 2-propanol, toluene, THF, methyl-THF or dimethoxyethane. The reaction temperature here is 60° C. to 140° C., preferably from 80° C. to 120° C.

The reaction time is generally 4 to 24 hours, depending on the composition of the mixture and the selected temperature range. The resulting compound of the formula 17 is then crystallized from the reaction mixture using a suitable solvent or solvent mixture, for example methanol, ethanol, 2-propanol, methyl tert-butyl ether or diisopropyl ether.

16

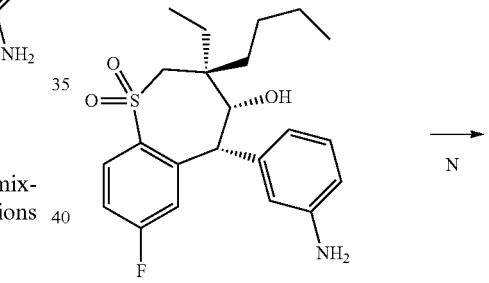

17

The compounds of the formula 17a, 17b and 17c or mixtures thereof are produced analogously to the conditions specified for the compound of the formula 17.

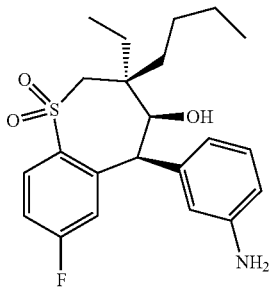

17a

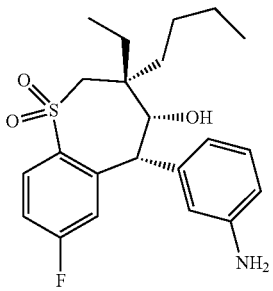

17b

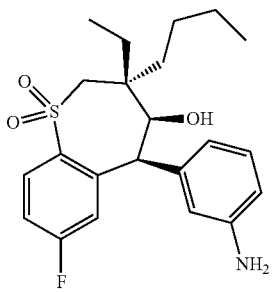

17c

Alternatively, the method for compound 17 or 17a/17b and 17c can be carried out as follows:

The compound of the formula 31 can be produced for example by reacting the compound of the formula 15 with dimethylamine in a suitable solvent, such as e.g. methanol, ethanol, 2-propanol, toluene, THF, methyl-THF or dimethoxyethane. The reaction temperature here is 60° C. to 140° C., preferably from 80° C. to 120° C.

The reaction time is generally 4 to 24 hours, depending on the composition of the mixture and the selected temperature range. The resulting compound of the formula 31 is then crystallized from the reaction mixture using a suitable solvent or solvent mixture, for example methanol, ethanol, 2-propanol, methyl tert-butyl ether or diisopropyl ether, or further reacted without purification.

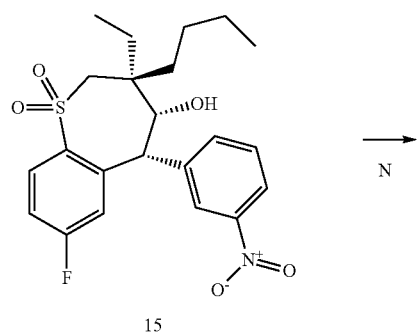

15

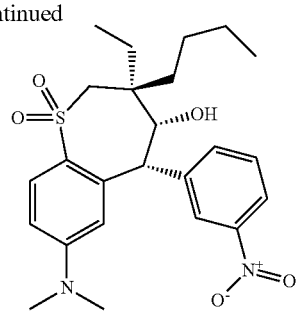

31

The compounds of the formula 31a, 31b and 31c or mixtures thereof are produced analogously to the conditions specified for the compound of the formula 31.

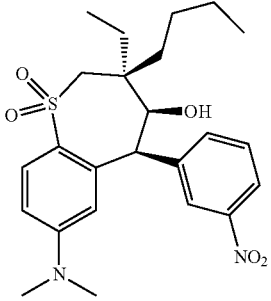

31a

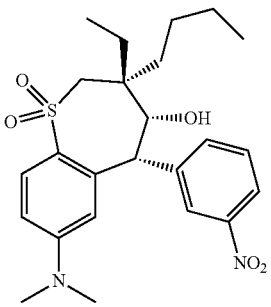

31b

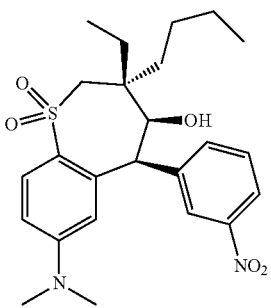

31c

The compound of the formula 17 can be produced, for example, by reacting the compound of the formula 31 with a suitable reducing agent, such as hydrogen/palladium on activated carbon in a suitable solvent, such as e.g. methanol, ethanol, 2-propanol, dichloromethane, toluene, THF, methyl-THF or dimethoxyethane. The reaction temperature here is 0° C. to 80° C., preferably from 20° C. to 50° C.

The reaction time is generally 2 to 12 hours, depending on the composition of the mixture and the selected temperature range. The resulting compound of the formula 17 is then crystallized from the reaction mixture using a suitable solvent or solvent mixture, for example methanol, ethanol, 2-propanol, methyl tert-butyl ether or diisopropyl ether.

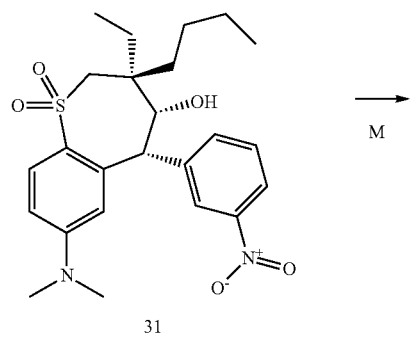

31

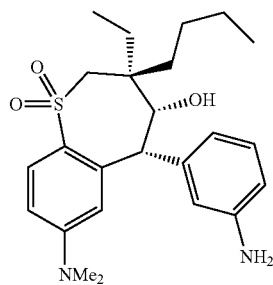

17

Compound 17 can be used further as follows for the production of the compounds of the formula I.

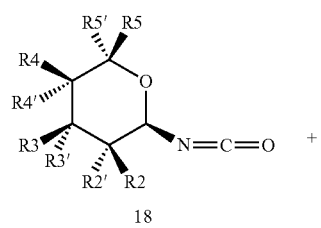

18

+

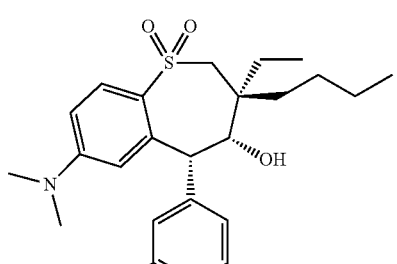

17

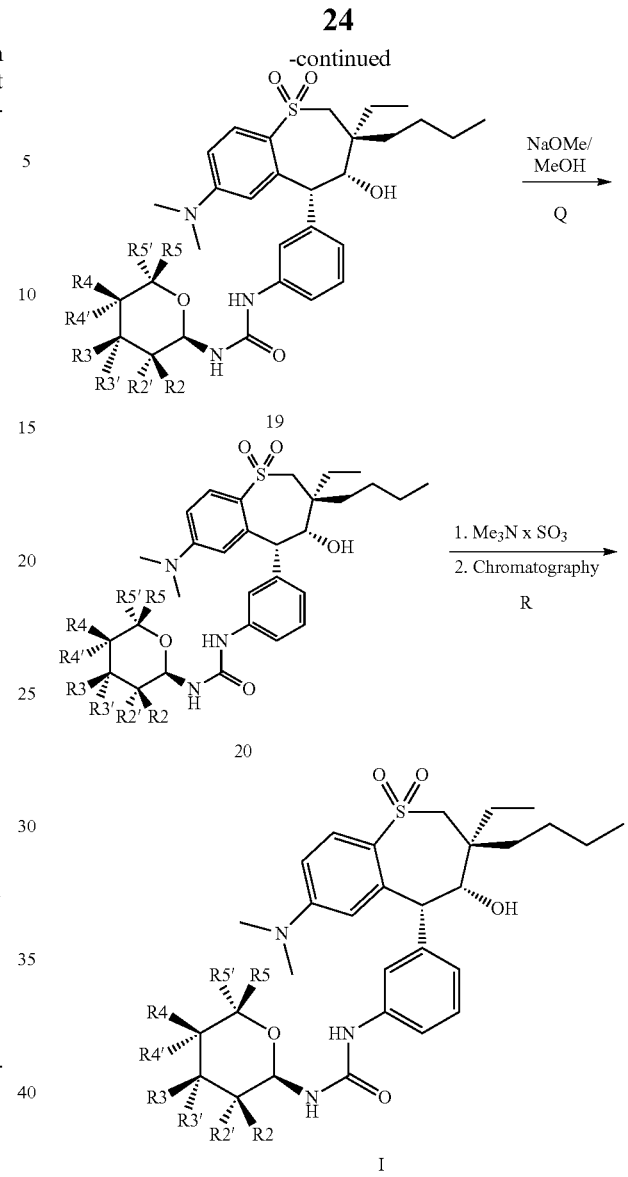

Compound 17a can further be used as follows for the production of the compound of the formula Ia.

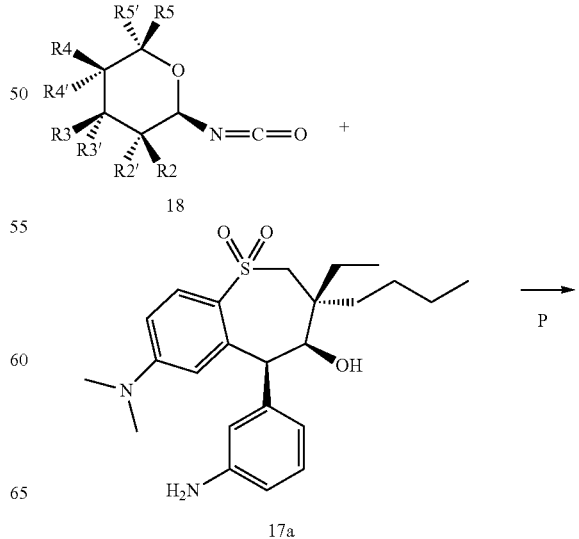

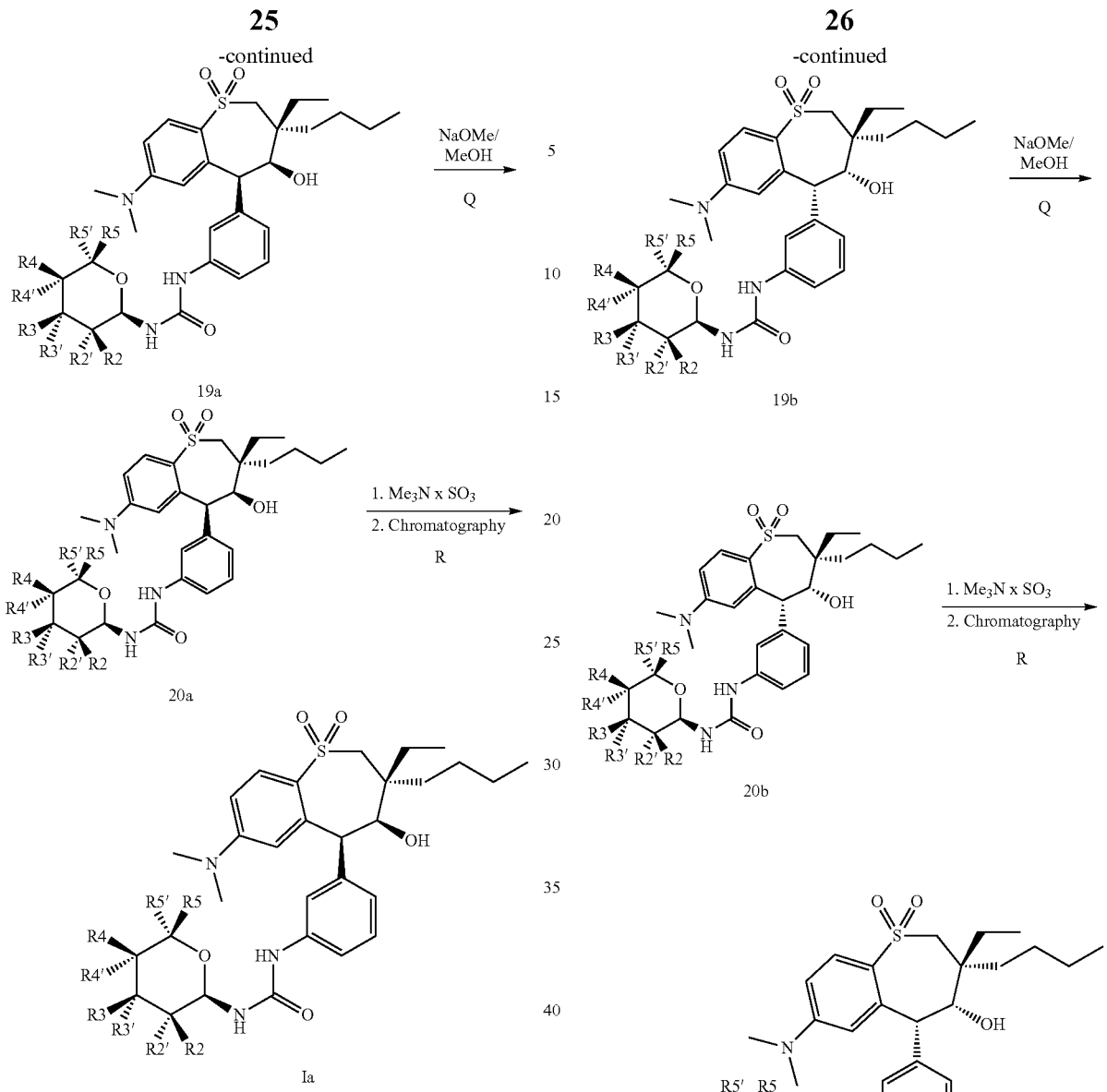
Compound 17b can further be used as follows for the production of the compound of the formula Ib.
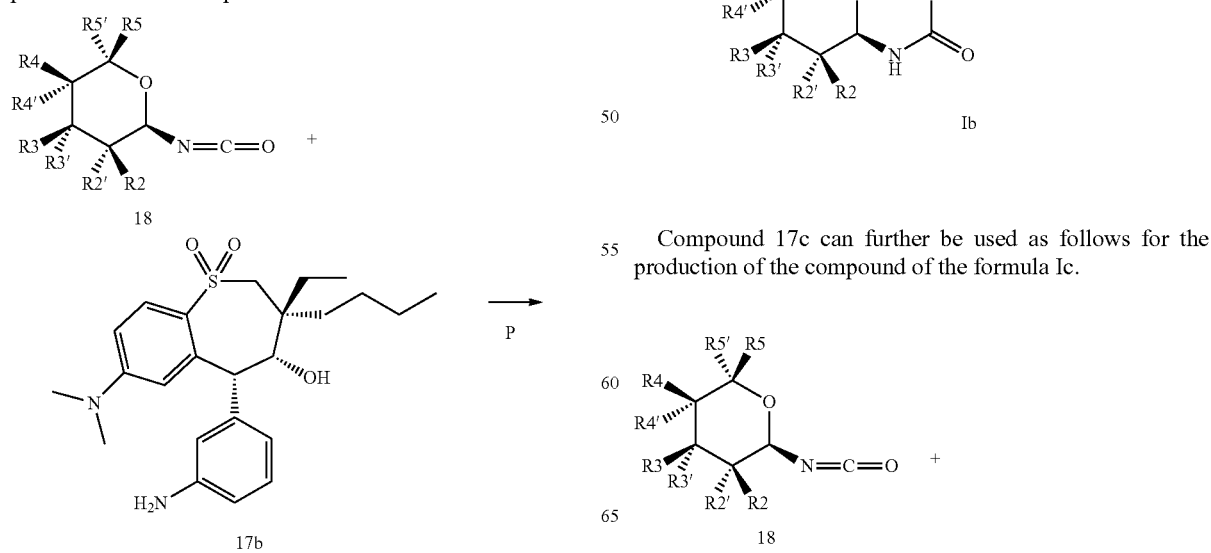
Compound 17c can further be used as follows for the production of the compound of the formula Ic.

In a preferred embodiment, compound 17 is used for the production of the compound 53.
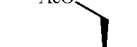

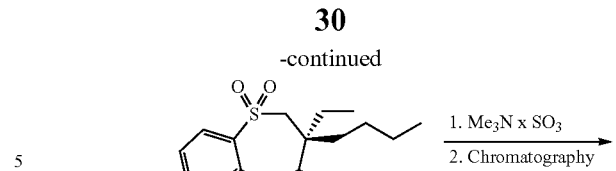

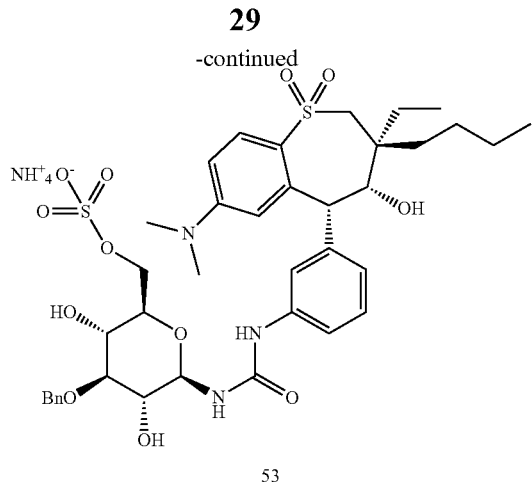

The compound 53a is produced e.g. in an analogous manner:

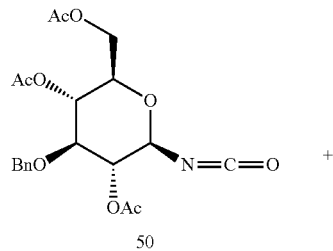

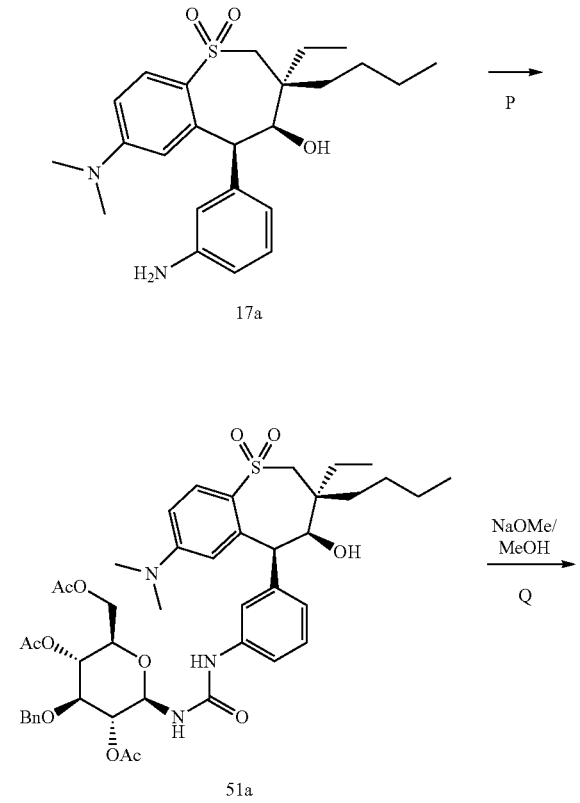

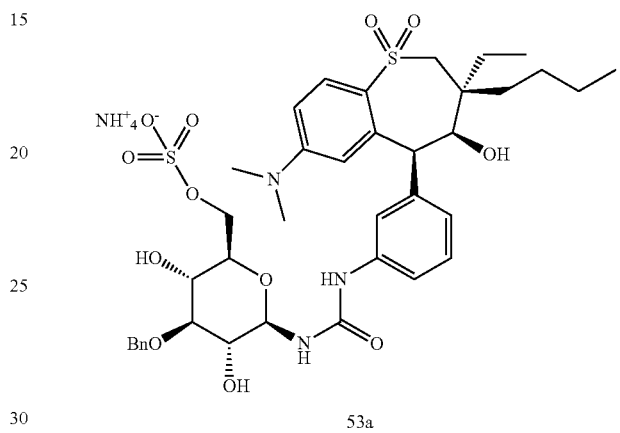

The examples listed below serve to illustrate the invention without, however, limiting it.

The compounds given in the table can be produced by the above method.

TABLE 1

| Ex. | R2, R2' | R3, R3' | R4, R4' | R5, R5' |
|---|---|---|---|---|
| 1 | OH, H | OBn, H | OH, H | CH₂OH, H |
| 2 | OH, H | OBn, H | OH, H | CH₂OH, H |
| 3 | OH, H | OBn, H | OH, H | CH₂OBn, H |
| 4 | OH, H | OBn, H | OH, H | CH₂OSO₂OH, H |
| 5 | OH, H | OBn, H | OSO₂OH, H | CH₂OSO₂OH, H |
| 6 | OH, H | OBn, H | OH, H | CH₂OSO₂OH, H |

Et = Ethyl, Bu = n-Butyl, Bn = Benzyl

The production of a number of examples is described in detail below; the other compounds of the formula I, Ia, Ib and Ic were obtained analogously:

EXPERIMENTAL SECTION

Example 1

Formula 52

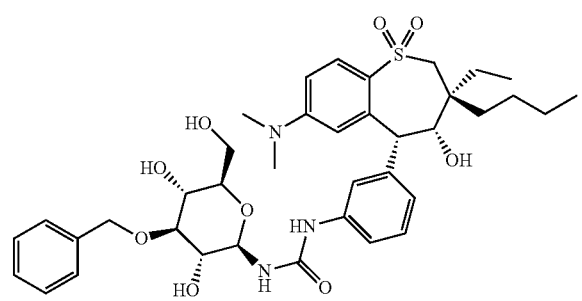

Synthesis of Example 1

Process Step A

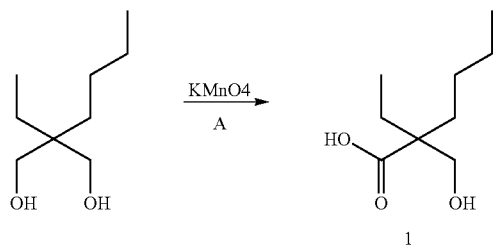

Process Step B

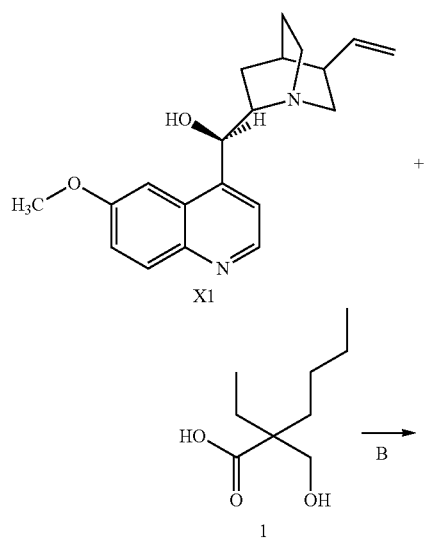

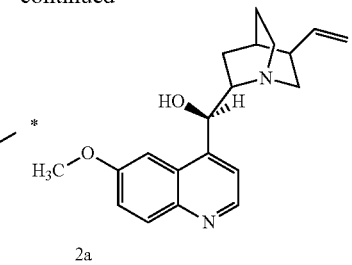

35.5 g (204 mmol) of the carboxylic acid of the formula 1 and 63 g (194 mmol; 0.95 eq.) of quinine are suspended in 440 ml of n-butyl acetate and 220 ml of n-heptane. The mixture is heated to 90° C. and stirred at this temperature for 15 minutes. The mixture is then cooled to 55° C., then to room temperature over the course of 12 hours and 2a is filtered off from the crystallized quinine salt of the formula 1.
Yield: 62 g (52%)
ee: 58% (RT: 6 minutes; Chiralpak AD 250×4.6; n-heptane/ethanol 25:1; 30° C.)
62 g of the quinine salt of the formula 2a are dissolved in 400 ml of n-butyl acetate and 400 ml of n-heptane at 100 to 110° C. and slowly cooled to room temperature overnight. It is drawn off from the precipitated solid of the formula 2a with suction and dried in vacuo.
Yield: 43 g (70%)
ee: 94% (RT: 6 minutes; Chiralpak AD 250×4.6; n-heptane/ethanol 25:1; 30° C.)
Process Step C:

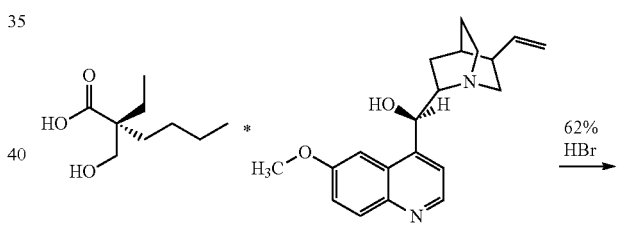

26 g of the quinine salt of the formula 2a are stirred in 110 ml of 62% strength HBr for 12 hours at 100° C. Afterwards, the conversion is complete (TLC ethyl acetate/n-heptane 1:1). The solution is cooled and admixed with 100 ml of water and 100 ml of toluene. The aqueous phase is separated off and the toluene phase is dried and distilled off in vacuo. The carboxylic acid of the formula 3 is purified by means of a short-path distillation at 2 mbar and jacket temperature of 140° C.
Yield: 11.1 g (90%)
$^1$H-NMR (CDCl$_3$): 3.83 (s, 2H); 2.98 (s, 2H); 2.32 (s, 3H); 2.15 (s, 3H); 1.6-1.8 (m, 4H); 1.1-1.4 (m, 4H); 0.85 (t, 3H); 0.8 (t, 3H)
Alternative process step to give compound 35a where R is methyl.

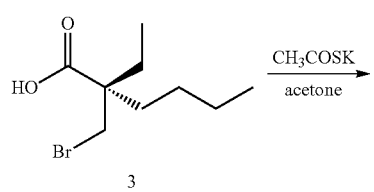

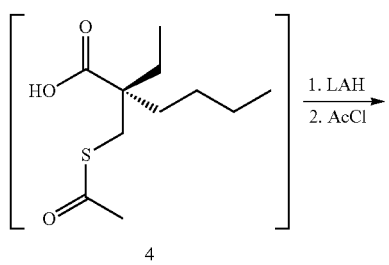

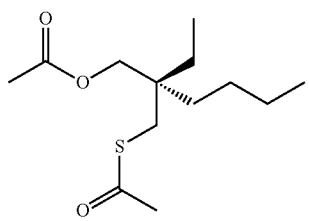

64 g (0.56 mol; 1.12 eq.) of potassium thioacetate are suspended in 400 ml of acetone. 118.57 g (0.5 mol) of the bromide of the formula 3, dissolved in 100 ml of acetone, are added and the solution is stirred at room temperature for 4 hours. The suspension is diluted with 1500 ml of toluene and filtered over 100 g of silica gel. The filtrate is concentrated by evaporation in vacuo to a volume of 1000 ml, cooled to 0° C. and slowly admixed with 750 ml (0.75 mol) of a 1M LAH solution in THF. The solution is stirred for 1-2 hours at 0° C. and overnight at RT. The solution is cooled to 10° C. and slowly admixed with 225 ml of acetyl chloride. The mixture is after-stirred for 1 hour and then admixed with 250 ml of toluene and 500 ml of water. The phases are separated and the aqueous phase is extracted again with 200 ml of toluene. The combined toluene phases are dried over sodium sulfate and the solvent is distilled off in vacuo. This gave the compound of the formula 35a (R is methyl).

Yield: 123 g (90%)

$^1$H-NMR (CDCl$_3$): 3.83 (s, 2H); 2.98 (s, 2H); 2.32 (s, 3H); 2.15 (s, 3H); 1.6-1.8 (m, 4H); 1.1-1.4 (m, 4H); 0.85 (t, 3H); 0.8 (t, 3H)

Process Steps D and E:

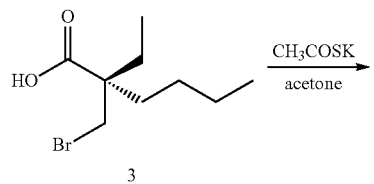

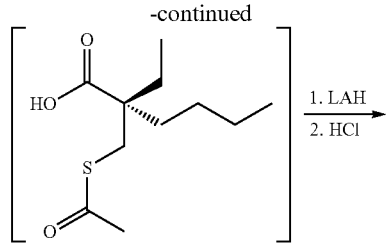

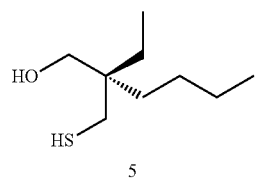

64 g (0.56 mol; 1.12 eq.) of potassium thioacetate are suspended in 400 ml of acetone. 118.57 g (0.5 mol) of the bromide of the formula 3, dissolved in 100 ml of acetone, were added and the solution was stirred for 4 hours at room temperature. The suspension is diluted with 1500 ml of toluene and filtered over 100 g of silica gel. The filtrate is concentrated by evaporation in vacuo to a volume of 1000 ml, cooled to 0° C. and slowly admixed with 750 ml (0.75 mol) of a 1M LAH solution in THF. The solution is stirred for 1-2 hours at 0° C. and overnight at RT. The solution is cooled to 10° C. and slowly admixed with 700 ml of 2N hydrochloric acid. The mixture is after-stirred for 1 hour and then diluted with 250 ml of toluene. The phases are separated and the aqueous phase is extracted again with 200 ml of toluene. The combined toluene phases are dried over sodium sulfate and the solvent is distilled off in vacuo. This gave the compound of the formula 5.

Yield: 103 g (90%)

$^1$H-NMR (CDCl$_3$): 3.83 (s, 2H); 2.98 (s, 2H); 1.6-1.8 (m, 4H); 1.1-1.4 (m, 4H); 0.85 (t, 3H); 0.8 (t, 3H)

Process Step F:

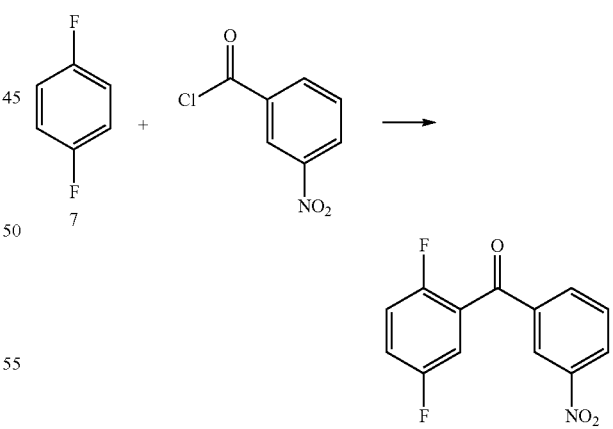

Over the course of 30 minutes at an internal temperature of 20° C., 38.4 g of anhydrous aluminum chloride are added to a mixture of 20 g of 3-nitrobenzoyl chloride and 54 ml of 1,4-difluorobenzene, during which the temperature increases to 30° C. The reaction mixture is heated under reflux for 16 hours. Afterwards, the reaction is complete (TLC control with toluene/AcOEt/CH3CO2H 95:5:3).

The reaction mixture is cooled to 50° C. and admixed with 40 ml of ethyl acetate. The suspension is poured onto a mixture of 180 ml of water and 30 ml of 2N hydrochloric acid. The phases are separated and the aqueous phase is after-extracted with ethyl acetate. The combined organic phases are dried over sodium sulfate and the solvent is evaporated in vacuo. The 2,4-difluoro-3'-nitrobenzophenone of the formula 8 is crystallized from the remaining residue using 2-propanol.

Yield: 24.6 g (86.6%)

$^1$H-NMR (CDCl$_3$): 8.63 (s, 1H); 8.49 (d, 1H); 8.15 (d, 1H); 7.71 (t, 1H); 7.15-7.45 (m, 3H)

Alternative process step with compound 35a (R is methyl)

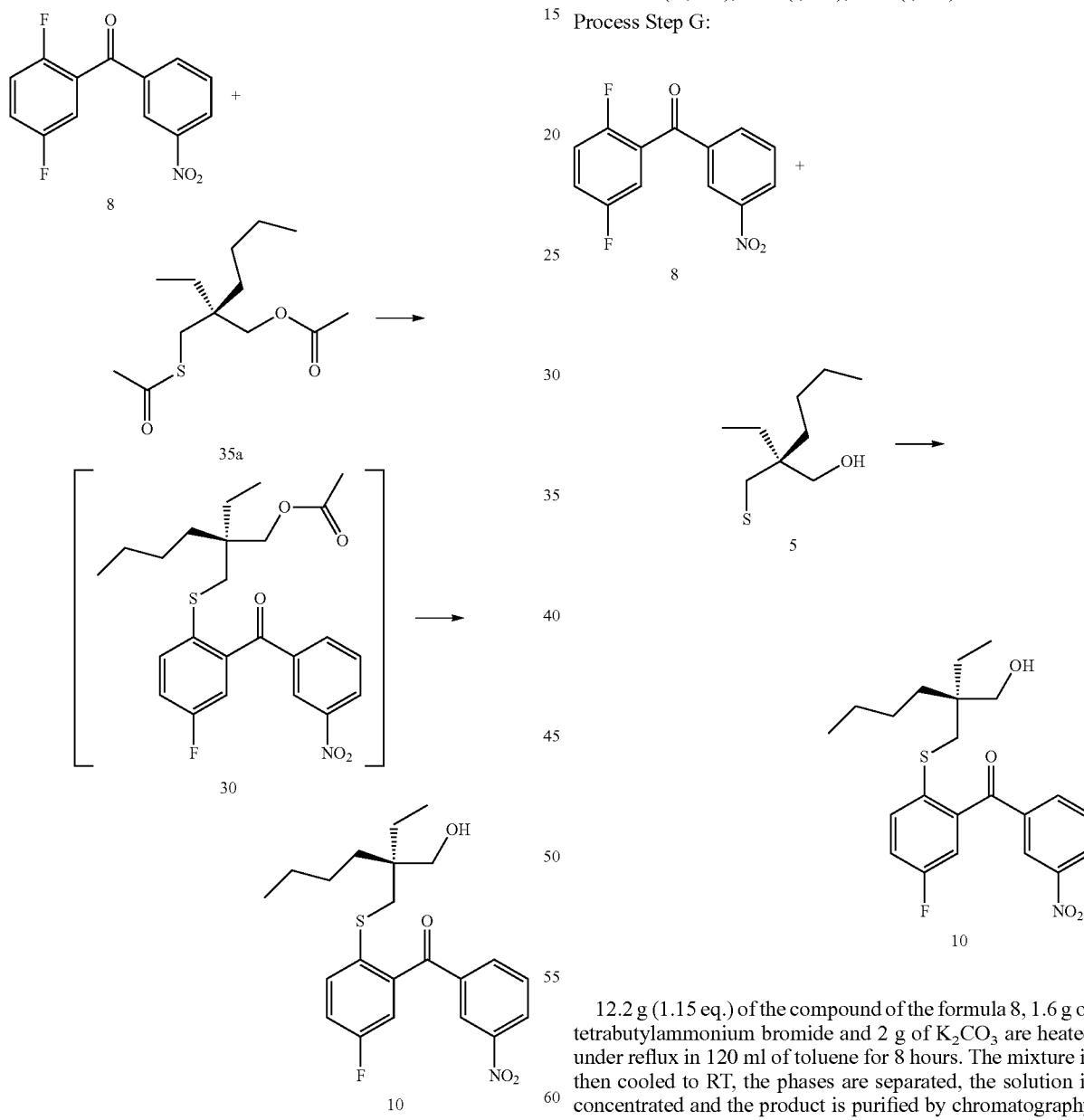

14.4 g (1.15 eq.) of the compound of the formula 8 and 1.9 g of tetrabutylammonium bromide are dissolved in 80 ml of toluene and 70 ml of a 2M K$_2$CO$_3$ solution. The mixture is heated under reflux and, over the course of 24 hours, admixed with 14.5 g of the compound of the formula 35a, dissolved in 30 ml of toluene. The reaction mixture is heated for a further 12 hours. The mixture is then cooled to RT, the phases are separated and the organic phase is briefly distilled in order to remove residual amounts of water. 10 ml of methanol and 2.5 ml of 30% strength sodium methylate solution are added and the mixture is stirred for 1.5 hours. The solution is then concentrated and the product is purified by chromatography (eluent: dichloromethane). This gave the compound of the formula 10.

Yield: 10.1 g (57% based on compound 35a)

$^1$H-NMR (CDCl$_3$): 8.53 (s, 1H); 8.49 (d, 1H); 8.15 (d, 1H); 7.71 (t, 1H); 7.60-7.68 (m, 1H); 3.45 (d, 2H); 2.83 (s, 2H); 1.05-1.35 (m, 8H); 0.85 (t, 3H); 0.75 (t, 3H)

Process Step G:

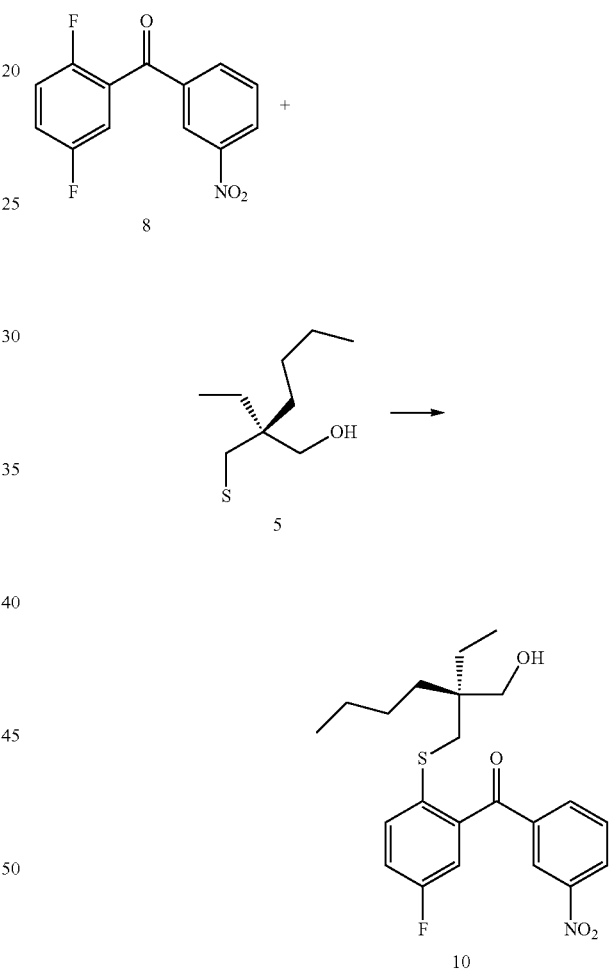

12.2 g (1.15 eq.) of the compound of the formula 8, 1.6 g of tetrabutylammonium bromide and 2 g of K$_2$CO$_3$ are heated under reflux in 120 ml of toluene for 8 hours. The mixture is then cooled to RT, the phases are separated, the solution is concentrated and the product is purified by chromatography (eluent: dichloromethane). This gave the compound of the formula 10.

Yield: 6.9 g (46% based on compound 35a, pale yellow oil)

$^1$H-NMR (CDCl$_3$): 8.53 (s, 1H); 8.49 (d, 1H); 8.15 (d, 1H); 7.71 (t, 1H); 7.60-7.68 (m, 1H); 3.45 (d, 2H); 2.83 (s, 2H); 1.05-1.35 (m, 8H); 0.85 (t, 3H); 0.75 (t, 3H)

Process Step H:

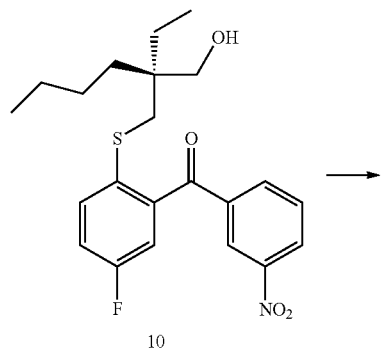
10

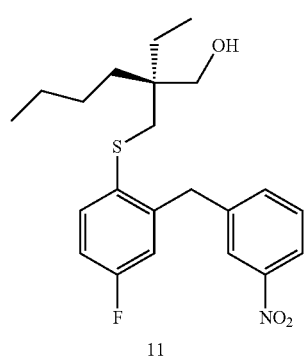
11

11 g of the compound of the formula 11, 20 g of triethylsilane and 25 g of boron trifluoride diethyl ether complex are stirred for 8 hours at an internal temperature of 65° C. Afterwards, the reduction is complete (TLC: toluene/ethyl acetate 10:1). The reaction solution is cooled to RT and slowly admixed with 50 ml of a 2M sodium carbonate solution. 100 ml of ethyl acetate are then added, the organic phase is concentrated by evaporation in vacuo and the product, the compound of the formula 11, is purified by chromatography (eluent: toluene/ethyl acetate 10:1).

Yield: 9.6 g (90.5%, pale yellow oil)

Rf=0.4. $C_{22}H_{28}FNO_3S$ (405.54). MS (M+H)+=406.54

Process Step I:

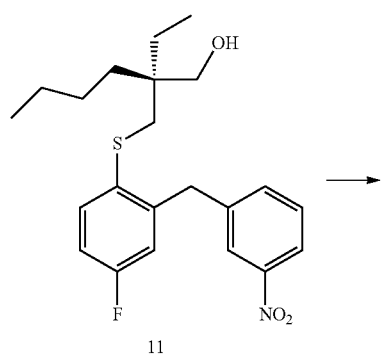
11

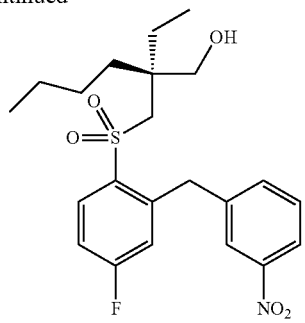
12

4 g of potassium carbonate and 12 g of the compound of the formula 11 are dissolved in 80 ml of ethanol, 20 ml of acetonitrile and 20 ml of water. The solution is cooled to 5° C. and admixed with 24 ml of 30% strength $H_2O_2$ over the course of 1 hour. The solution is stirred overnight and admixed with 100 ml of water to precipitate the crude product. The crude product is filtered off, washed with water and crystallized from diisopropyl ether. This gave the compound of the formula 12.

Yield: 11.65 g (90%)

$^1$H-NMR (CDCl$_3$): 8.05-8.15 (m, 3H); 7.55-7.65 (m, 2H); 7.08-7.15 (m, 1H); 6.90-7.00 (m, 1H); 4.60 (s, 2H); 3.60-3.75 (m, 2H); 2.95 (s, 2H); 1.05-1.45 (m, 8H); 0.85 (t, 3H); 0.75 (t, 3H)

Process Step J:

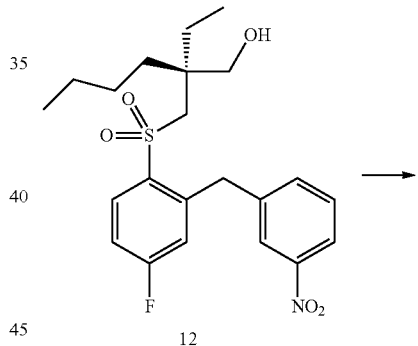
12

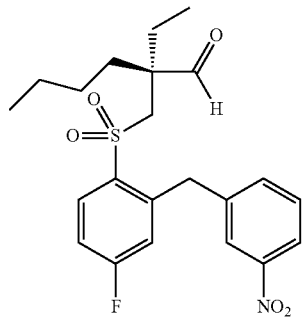
13

11.75 g (27 mmol) of the compound of the formula 12 and 0.128 g (0.022 eq.) of 4-acetamido-TEMPO (4-acetamido-2,2,6,6-tetramethylpiperidin-1-oxyl) are dissolved in 160 ml of dichloromethane. 1.5 g of NaBr (0.54 eq.), dissolved in 25 ml of water, and 4.45 kg (2 eq.) of NaHCO$_3$, dissolved in 100 ml of water, are added. 20.1 g (1.32 eq.) of a 12.9% strength NaOCl are metered in continuously over the course of 2 hours. The reaction mixture is after-stirred for a further 15 minutes and the complete conversion is monitored via TLC (heptane/ethyl acetate 2:1). Following aqueous work-up, the aldehyde of the formula 13 is crystallized with diisopropyl ether.

Yield: 10.5 g (90%)

$^1$H-NMR (400 MHz, CDCl$_3$): 9.45 (s, 1H); 8.05-8.15 (m, 3H); 7.55-7.65 (m, 2H); 7.08-7.15 (m, 1H); 6.90-7.00 (m, 1H); 4.60 (s, 2H); 3.20 (s, 2H); 1.55-2.05 (m, 4H); 1.05-1.35 (m, 4H); 0.85 (t, 3H); 0.75 (t, 3H)

Process Step K and L:

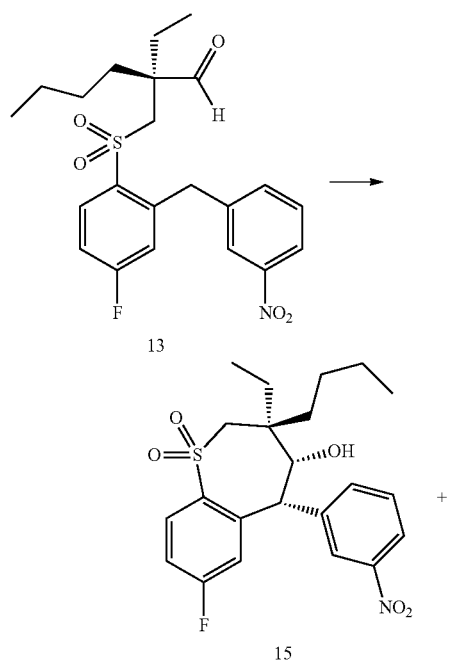

A solution of 9.3 g (21.4 mmol) of the aldehyde of the formula 13 in 80 ml of THF is admixed at 0° C. with 4.1 ml (0.18 eq.) of a 1M KOtBu in THF and after-stirred for 1 hour at this temperature. The reaction solution is neutralized with 0.25 g of acetic acid (4.1 mmol, 0.18 eq.) and concentrated by evaporation in vacuo. The two isomers (the compounds of the formulae 15 and 15A) are separated by chromatography over silica gel (eluent: toluene/ethyl acetate 5:1).

Yield of compound of the formula 15: 4.1 g (45%, pale yellow solid)

Rf=0.38. C$_{22}$H$_{26}$FNO$_5$S (435.52). MS (M+H)+=436.52

Yield of compound of the formula 15A: 3.8 g (41%, pale yellow solid)

Rf=0.49. C$_{22}$H$_{26}$FNO$_5$S (435.52). MS (M+H)+=436.52

Compounds of the Formulae 17 and 17A

Method A:

Process Step M:

Production of the Compound of the Formula 16:

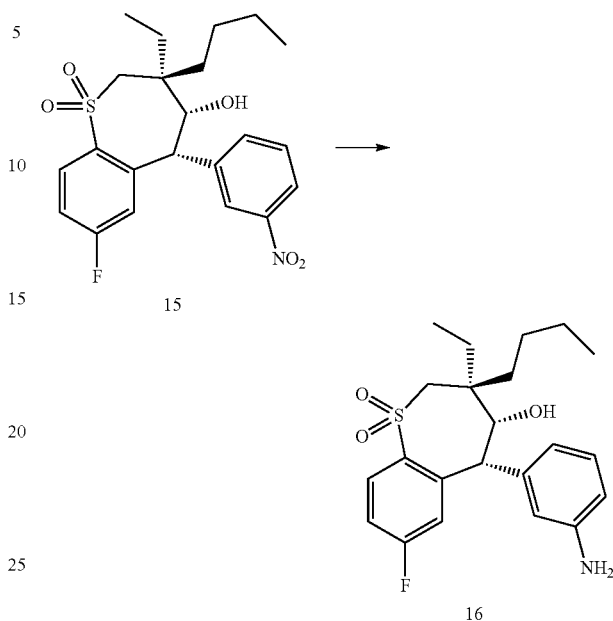

4 g of the compound of the formula 15 are dissolved in 40 ml of dichloromethane/ethanol 1:1, admixed with 400 mg of Pd/C$_5$% and hydrogenated until the end of the hydrogen absorption (3-4 hours) at 3 bar (TLC control: ethyl acetate/n-heptane 2:1). The catalyst is filtered off and the solvent is distilled off in vacuo. This gave the compound of the formula 16.

Yield: 3.7 g (98%)

Rf=0.48. C$_{22}$H$_{26}$FNO$_3$S (405.54). MS (M+H)+=406.54

Process step N:

Production of the Compound of the Formula 17:

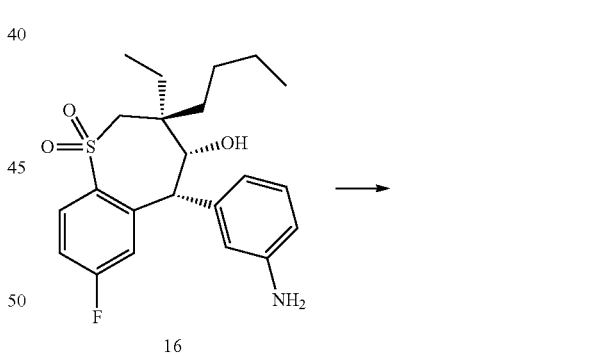

8 g of the compound 16 are introduced as initial charge in a pressurized container and admixed with 50 ml of a 33% strength solution of dimethylamine in ethanol. The pressurized container is sealed gas-tight and the solution is heated at 120° C. for at least 8 hours. The solution is cooled and slowly admixed with water (10 ml) for crystallization. Once crystallization has taken place, a further 50 ml of water is added for complete precipitation and the suspension is stirred for 1 hour. The aniline (compound 17) is filtered off, washed thoroughly with water and dried in vacuo.

Yield: 7.8 g (91%, colorless solid)

$^1$H-NMR (400 MHz, CDCl$_3$): 7.90 (d, 1H); 7.18 (t, 1H); 6.92 (d, 1H, b); 6.80 (s, 1H, b); 6.63-6.67 (m, 1H); 6.45-6.53 (m, 1H); 6.10 (s, 1H, b); 5.43 (s, 1H); 4.13 (s, 1H); 3.12 (d, 1H); 2.98 (d, 1H); 2.82 (s, 6H); 2.15-2.25 (m, 1H); 1.10-1.65 (m, 8H); 0.90 (t, 3H); 0.85 (t, 3H)

$C_{24}H_{34}N_2O_3S$ (437.54). MS (M+H)+=438.54

Method B:

Yield: 4.76 g (90%)

$C_{24}H_{32}N_2O_5S$ (460.6). MS (M+H)+=461.6

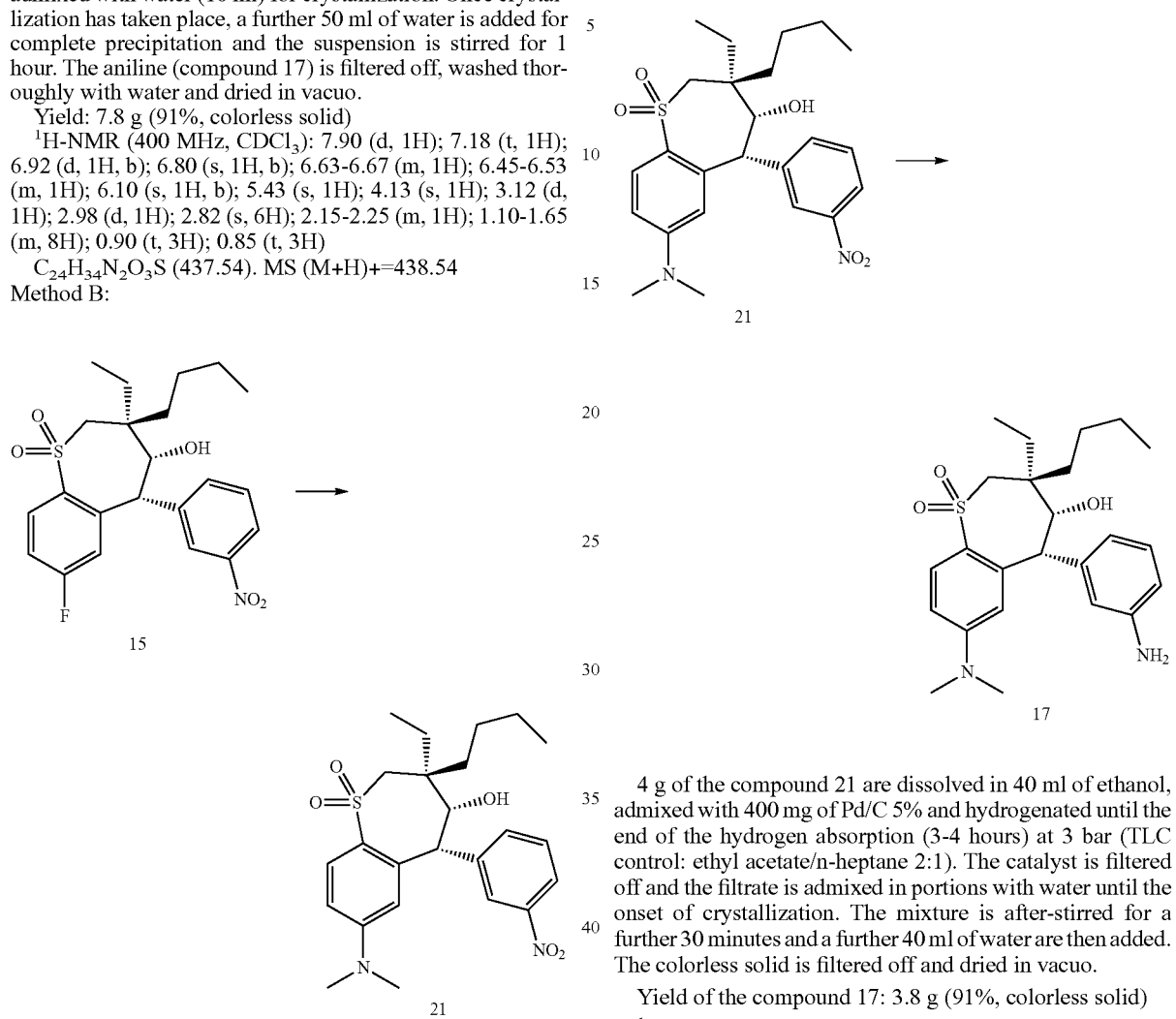

5 g of the compound 15 are introduced as initial charge in a pressurized container and admixed with 50 ml of a 33% strength solution of dimethylamine in ethanol. The pressurized container is sealed gas-tight and the solution is heated at 120° C. for at least 8 hours. The solvents are evaporated off and the residue is chromatographed over silica gel (eluent: ethyl acetate/n-heptane 2:1).

4 g of the compound 21 are dissolved in 40 ml of ethanol, admixed with 400 mg of Pd/C 5% and hydrogenated until the end of the hydrogen absorption (3-4 hours) at 3 bar (TLC control: ethyl acetate/n-heptane 2:1). The catalyst is filtered off and the filtrate is admixed in portions with water until the onset of crystallization. The mixture is after-stirred for a further 30 minutes and a further 40 ml of water are then added. The colorless solid is filtered off and dried in vacuo.

Yield of the compound 17: 3.8 g (91%, colorless solid)

$^1$H-NMR (400 MHz, CDCl$_3$): 7.90 (d, 1H); 7.18 (t, 1H); 6.92 (d, 1H, b); 6.80 (s, 1H, b); 6.63-6.67 (m, 1H); 6.45-6.53 (m, 1H); 6.10 (s, 1H, b); 5.43 (s, 1H); 4.13 (s, 1H); 3.12 (d, 1H); 2.98 (d, 1H); 2.82 (s, 6H); 2.15-2.25 (m, 1H); 1.10-1.65 (m, 8H); 0.90 (t, 3H); 0.85 (t, 3H)

$C_{24}H_{34}N_2O_3S$ (437.54). MS (M+H)+=438.54

Process Step P:

Production of the Compounds of the Formulae 51 and 52:

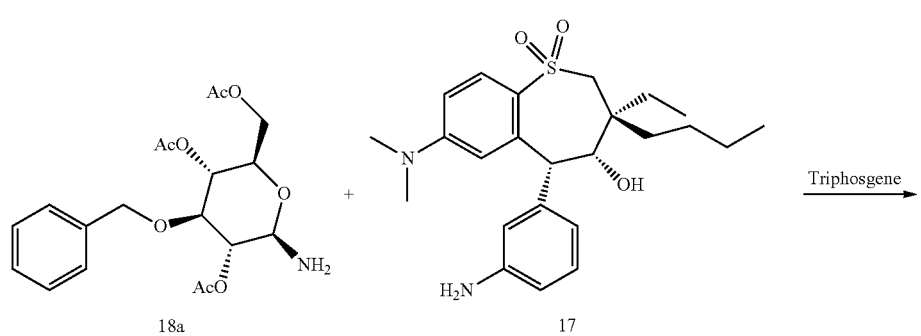

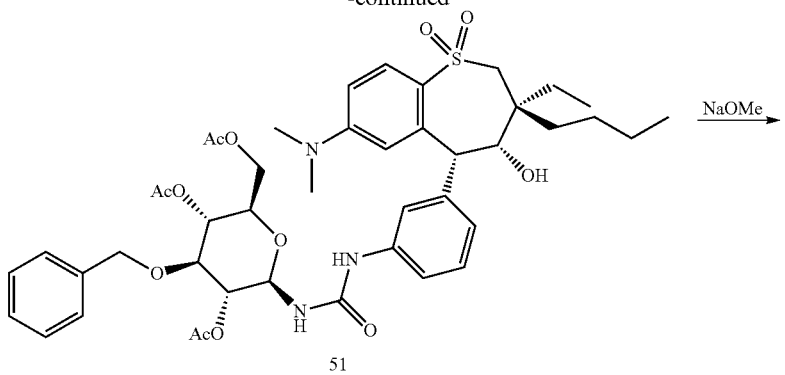

51

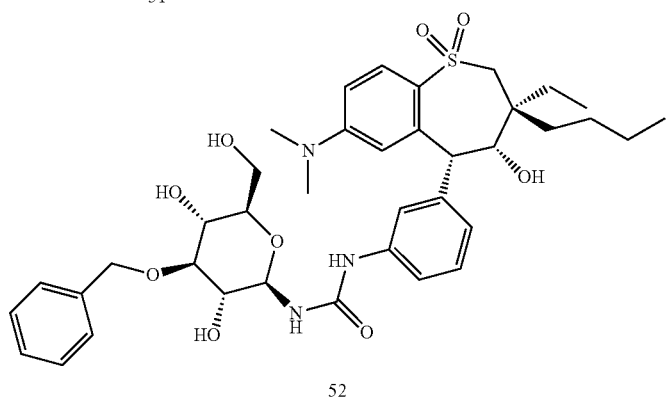

52

900 mg of triphosgene are dissolved in 10 ml of methylene chloride. Over the course of 20 minutes, a solution of 3.0 g (7.6 mmol) of amine of the formula 18a and 3 ml of N-ethylmorpholine in 20 ml of methylene chloride is added dropwise at room temperature to this solution. The mixture is then stirred for a further 1 hour and then a solution of 3.0 g (7.0 mmol) of aniline of the formula 17 (U.S. Pat. No. 5,994,391), dissolved in 20 ml of methylene chloride, is slowly added dropwise. After a further 30 minutes, the reaction is complete (TLC control). Washing is carried out twice with saturated sodium chloride solution, followed by filtration over silica gel and concentration by evaporation, giving 7 g of crude product of the formula 51. This is dissolved in 50 ml of methanol and admixed with 2 ml of 1 M sodium methanolate/methanol solution. After 30 minutes, the reaction solution is neutralized with 4 ml of 0.5 M HCL/methanol solution and concentrated by evaporation. The residue is purified using flash chromatography. Yield 4.72 g (93%) of the compound of the formula 52 as colorless solid. TLC (methylene chloride/methanol/conc. ammonia 30/5/1). $R_f$=0.7. $C_{38}H_{51}N_3O_9S$ (725.91). MS $(M+H)^+$=726.38.

Example 2 and 3

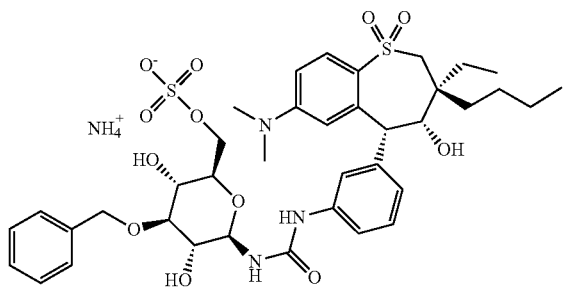

53

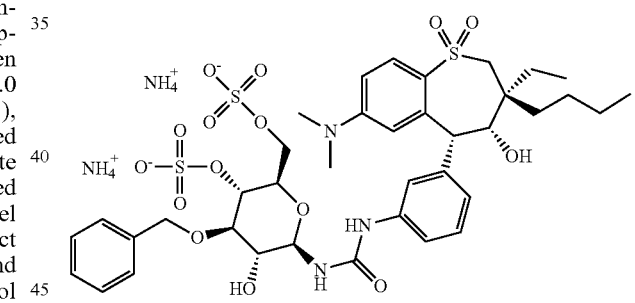

23

50.0 g (68.9 mmol) of example 52 are dissolved in 500 ml of pyridine and, after adding 17 g of pyridine-sulfur trioxide complex, the mixture is stirred for 30 minutes at 60° C. After adding 400 ml of methanol, the mixture is concentrated by evaporation on a rotary evaporator. The residue is again evaporated with 300 ml of methanol and then purified by means of flash chromatography. Yield 38.4 g (68%) of the compound of the formula Ia as ammonium salt. TLC (methylene chloride/methanol/conc. ammonia 30/5/1). $R_f$=0.4. $C_{38}H_{51}N_3O_{12}S_2 \times NH_3$ (823.00). MS $(M+H)^+$=804.21.

As by-product, 4.0 g (7%) of the disulfate of the formula 23 are obtained as double ammonium salt. TLC (methylene chloride/methanol/conc. ammonia 30/5/1). $R_f$=0.1.

$C_{38}H_{51}N_3O_{15}S_3 \times 2NH_3$ (920.09). MS $(M+H)^+$=886.45.

This disulfate can also be obtained as main product if twice the amount of sulfur trioxide complex is used.

Example 4

Formula 52a

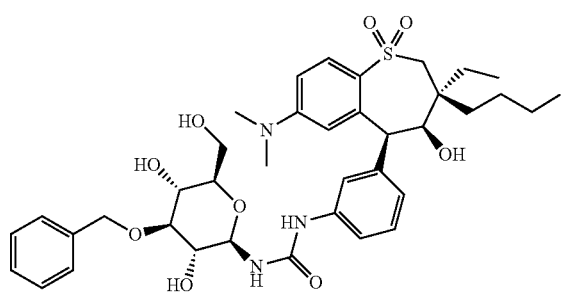

Process Step M:
Production of the Compound of the Formula 16A:

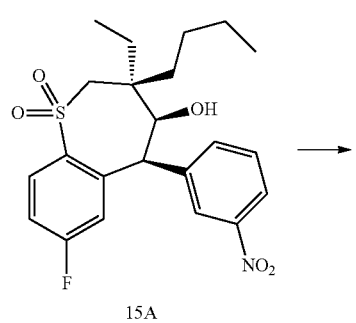

The compound 16A was produced analogously to compound 16.

Yield: 3.7 g (98%)

$^1$H-NMR (400 MHz, DMSO): 7.95 (m, 1H); 7.25 (t, 1H); 7.10 (t, 1H); 6.72 (d, 1H, b); 6.50-6.58 (m, 3H); 5.22 (d, 1H); 5.05-5.10 (m, 3H); 3.98 (d, 1H); 3.18 (d, 1H); 3.08 (d, 1H); 2.08-2.15 (m, 1H); 1.60-1.65 (m, 1H); 1.05-1.40 (m, 6H); 0.84 (t, 3H); 0.82 (t, 3H)

Process Step N:
Production of the Compound of the Formula 17A:

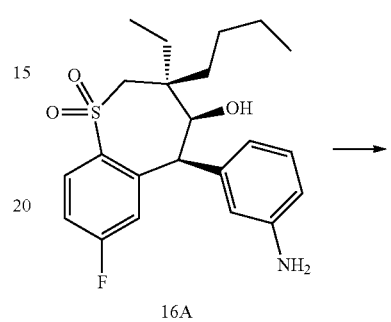

The compound 17A was produced analogously to compound 17.

Yield: 7.6 g (88%, colorless solid)

$^1$H-NMR (400 MHz, DMSO): 7.62 (d, 1H); 7.18 (t, 1H); 6.73 (d, 1H, b); 6.50-6.58 (m, 2H); 6.48 (d, 1H, b); 6.10 (s, 1H, b); 5.00-5.05 (m, 3H); 4.85 (d, 1H); 3.92 (d, 1H); 3.40-3.50 (m, 1H); 3.00 (d, 1H); 3.03 (d, 1H); 2.75 (s, 6H); 2.05-2.15 (m, 1H); 1.60-1.68 (m, 1H); 1.32-1.40 (m, 1H); 1.00-1.25 (m, 6H); 0.85 (t, 3H); 0.80 (t, 3H)

Process Step P:
Production of the Compound of the Formula 52a:

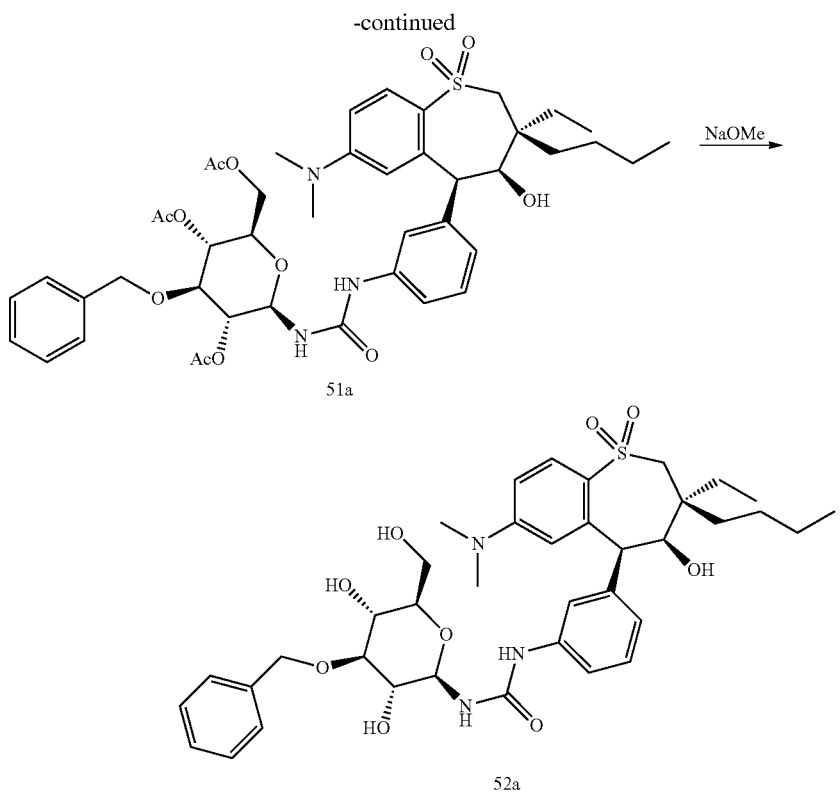

2.7 g of triphosgene are dissolved in 30 ml of methylene chloride. Over the course of 20 minutes, a solution of 9.0 g (22.8 mmol) of amine of the formula 18a and 9 ml of N-ethylmorpholine in 60 ml of methylene chloride is added dropwise at room temperature to this solution. The mixture is then stirred for a further 1 hour and then a solution of 9.0 g (21.0 mmol) of aniline of the formula 17a, dissolved in 50 ml of methylene chloride, is slowly added dropwise. After a further 30 minutes, the reaction is complete (TLC control). Washing is carried out twice with saturated sodium chloride solution, followed by filtration over silica gel and concentration by evaporation, giving 21 g of crude product of the formula 51a. This is dissolved in 100 ml of methanol and admixed with 5 ml of 1 M sodium methanolate/methanol solution. After 30 minutes, the reaction solution is neutralized with 10 ml of 0.5 M HCL/methanol solution and concentrated by evaporation. The residue is purified by means of flash chromatography. Yield 14 g (92%) of the compound of the formula 52a as colorless solid. TLC (methylene chloride/methanol/conc. ammonia 30/5/1). $R_f$=0.65. $C_{38}H_{51}N_3O_9S$ (725.91). MS $(M+H)^+$=726.38.

Example 5 and 6

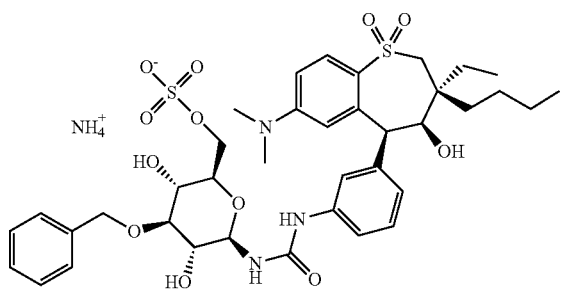

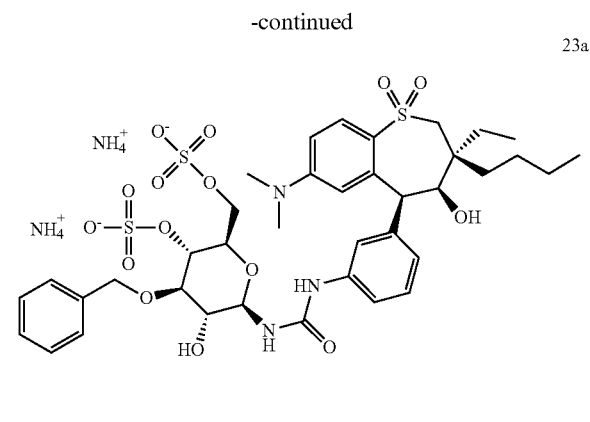

10.0 g (13.8 mmol) of example 52a are dissolved in 100 ml of pyridine and, after adding 3.5 g of pyridine-sulfur trioxide complex, the mixture is stirred for 30 minutes at 60° C. After adding 100 ml of methanol, the mixture is concentrated by evaporation on a rotary evaporator. The residue is evaporated again with 100 ml of methanol and then purified using flash chromatography. Yield 7 g (64%) of the compound of the formula 53a as ammonium salt. TLC (methylene chloride/methanol/conc. ammonia 30/5/1). $R_f$=0.35.

$C_{38}H_{51}N_3O_{12}S_2 \times NH_3$ (823.00). MS $(M+H)^+$=804.21.

As by-product, 0.8 g (7%) of the disulfate of the formula 23a is obtained as double ammonium salt. TLC (methylene chloride/methanol/conc. ammonia 30/5/1). $R_f$=0.1.

$C_{38}H_{51}N_3O_{15}S_3 \times 2NH_3$ (920.09). MS $(M+H)^+$=886.45.

This disulfate can also be obtained as main product if twice the amount of sulfur trioxide complex is used.

The invention claimed is:

1. A method for the production of the compound of the formula I

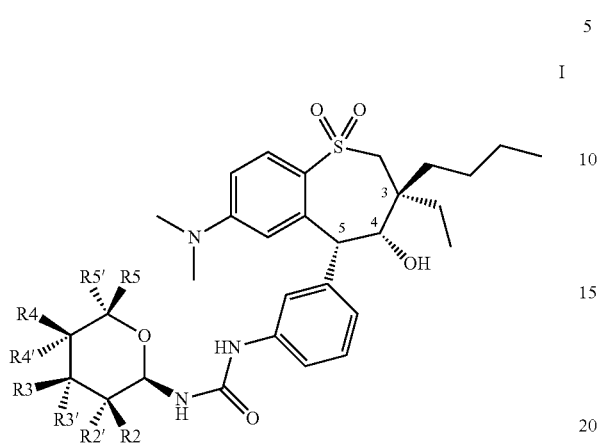

in which

R2, R2', R3, R3', R4, R4', R5, R5', independently of one another, are H, Cl, Br, I, OH, —(CH$_2$)—OH, CF$_3$, NO$_2$, N$_3$, CN, S(O)$_p$—R6, O—S(O)$_p$—R6, (C$_1$-C$_6$)-alkylene-S(O)$_p$—R6, (C$_1$-C$_6$)-alkylene-O—S(O)$_p$—R6, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, O—(C$_1$-C$_6$)-alkyl, where, in the alkyl radicals, one, more, or all hydrogen(s) can be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

where always at least one of the radicals R2, R2', R3, R3', R4, R4', R5, R5' has the meaning —O—(CH$_2$)$_m$-phenyl or —(CH$_2$)—O—(CH$_2$)$_m$-phenyl, where the phenyl ring may be mono- to trisubstituted with F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

R6 is H, OH, (C$_1$-C$_6$)-alkyl, NH$_2$, NH(C$_1$-C$_6$)-alkyl, N((C$_1$-C$_6$)-alkyl)$_2$;

n is 2, 3, 4, 5, 6;

m is 1, 2, 3, 4, 5, 6;

p is 0, 1, 2;

which comprises

G) reacting the compound of the formula 5

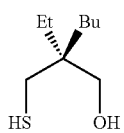

with a compound of the formula 8

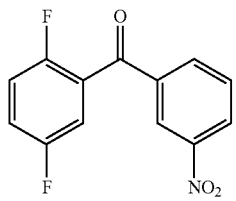

to give the compound of the formula 10

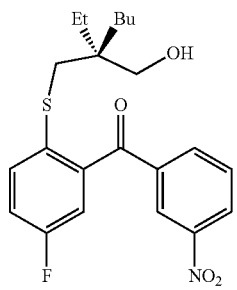

and then in a further process step

H) reacting the compound of the formula 10 in the presence of BF$_3$ and Et$_3$SiH to give a compound of the formula 11

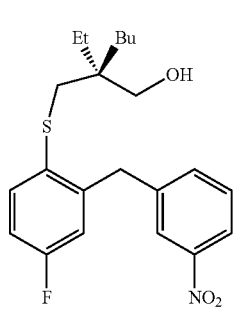

and then in a further process step

I) reacting the compound of the formula 11 in the presence of H$_2$O$_2$ to give compound 12

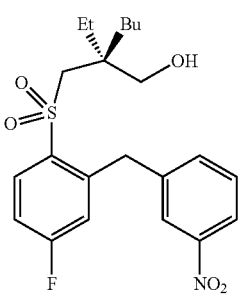

and then in a further process step

J) reacting the compound of the formula 12 in the presence of TEMPO (2,2,6,6-tetramethylpiperidinyloxyl) to give compound 13

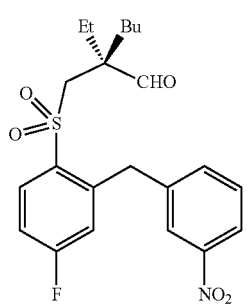

13 and then in a further process step
K) reacting the compound of the formula 13 in the presence of tBuOK in THF to give compound 15/15A

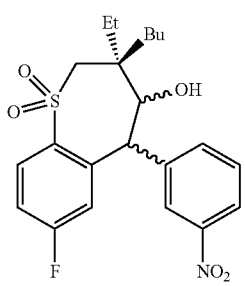

15/15A

2-Diastereoisomers
50:50 and then in a further process step
L) isolating the compound of the formula 15

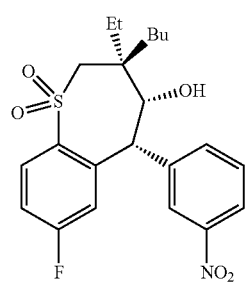

15 and then in a further process step
M) reacting the compound of the formula 15 with the help of H$_2$/Pd—C to give a compound of the formula 16

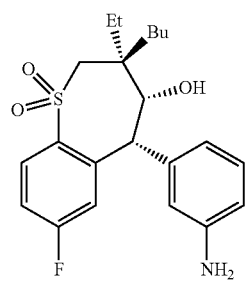

16 and then in a further process step
N) reacting the compound of the formula 16 in the presence of HNMe$_2$ to give a compound of the formula 17/17A

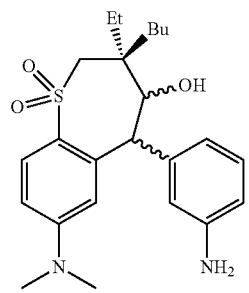

17/17A and then in a further process step
O) isolating the compound of the formula 17

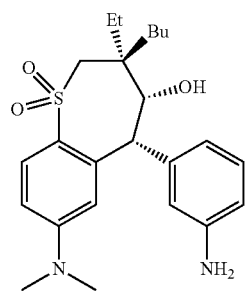

17 and then in a further process step
P) reacting the compound 17 with the compound 18, in which the radicals have the meanings given above

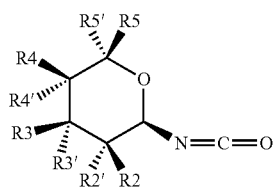

18 to give a compound of the formula 19

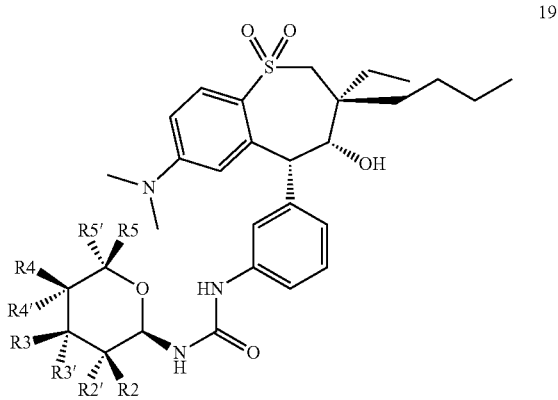

19 and then optionally in a further process step

Q) reacting the compound of the formula of the formula 19, in which the radicals have the meanings given above, to give a compound of the formula 20, in which the radicals have the meanings given above,

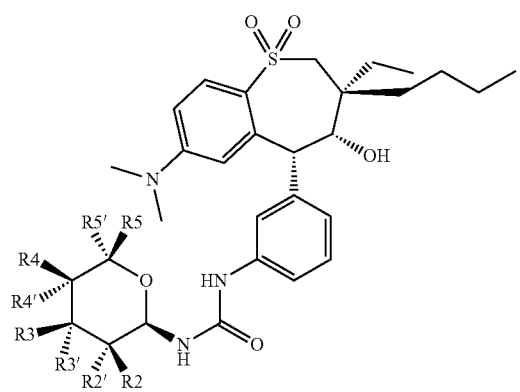

20 where any protective groups present are cleaved off, and then in then optionally in a further process step R) reacting the compound of the formula 20, in which the radicals have the meanings given above, to give a compound of the formula Ia, in which the radicals have the meanings given above,

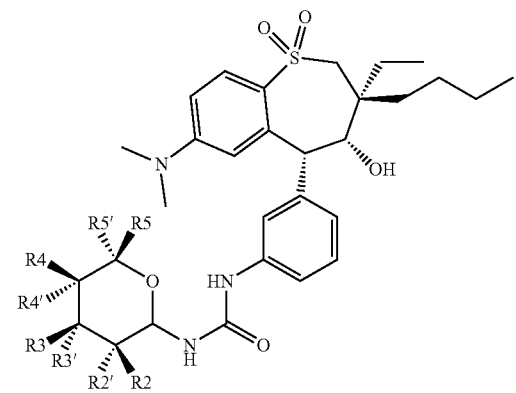

Ia as a result of which the substituents R2, R2', R3, R3', R4, R4', R5, R5' from formula 20 can be exchanged.

2. A method for the production of the compound of the formula 10

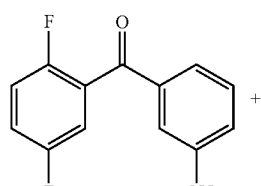

8

+

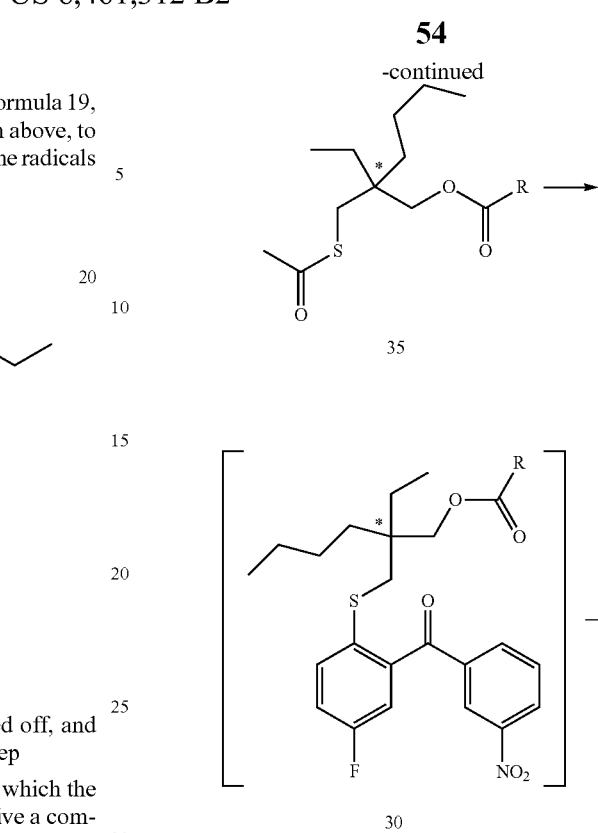

in which R in the compounds of the formulae 35 and 30 has the meaning $(C_1-C_6)$-alkyl, which comprises, in a first step, reacting the compound of the formula 8 with the compound of the formula 35 in the presence of an aqueous base and then, in a second step, completely converting the resulting mixture consisting of the compound of the formula 30 and the compound of the formula 10 to the compound of the formula 10 by alkaline hydrolysis.

3. The method for the production of the compound of the formula 10 as claimed in claim 2, wherein the aqueous base used is sodium carbonate, potassium carbonate or cesium carbonate.

4. A method for the production of the compound of the formula 11

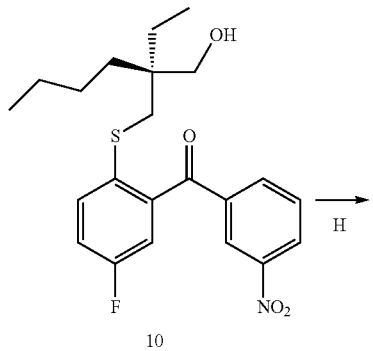

10 which comprises reacting the compound of the formula 10 with a suitable reducing agent to give the compound of the formula 11.

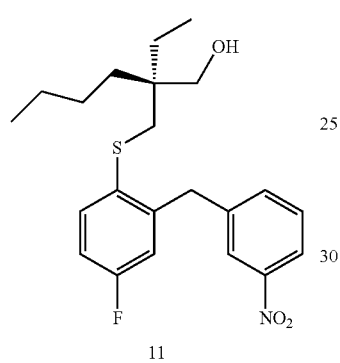

11

5. The method for the production of the compound of the formula 11 as claimed in claim 4, wherein hydrophosphorous acid/iodine, sodium borohydride/aluminum(III) chloride, triethylsilane/trifluoroacetic acid, isobutylaluminum dichloride, butylsilane/boron trifluoride, polyhydroxymethylsilane (PHMS) or triethylsilane/boron trifluoride is used as a suitable reducing agent.

6. A method for the production of the compound of the formula 12

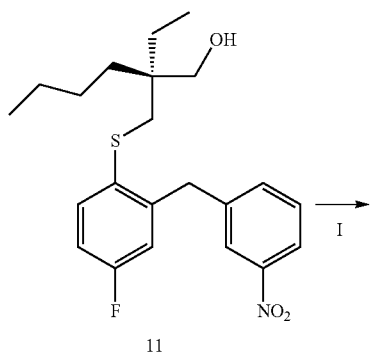

11

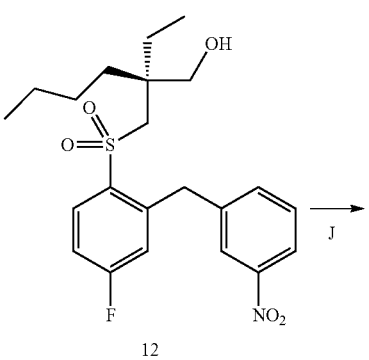

12 which comprises reacting the compound of the formula 11 with a suitable oxidizing agent to give the compound of the formula 12.

7. The method for the production of the compound of the formula 12 as claimed in claim 6, wherein sodium perborate, hydrogen peroxide/sodium tungstate, hydrogen peroxide/molybdenum(IV) oxide dichloride, ozones or hydrogen peroxide/acetonitrile/ethanol is used as suitable oxidizing agent.

8. A method for the production of the compound of the formula 13

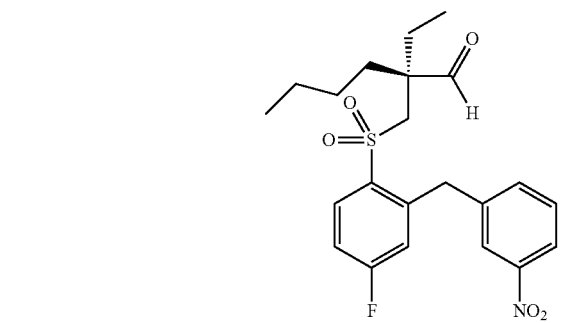

12

13 which comprises reacting the compound of the formula 12 with a suitable oxidizing agent to give the compound of the formula 12.

9. The method for the production of the compound of the formula 13 as claimed in claim 8, wherein oxalyl chloride/DMSO, sulfur trioxide-pyridine complex/DMSO, pyridinium dichromate, periodane or sodium hypochloride/TEMPO is used as suitable oxidizing agent.

10. The method for the production of the compound of the formula I as claimed in claim 1, wherein
R2, R2' R3, R3', R4, R4', R5, R5', independently of one another, are H, OH, —(CH$_2$)—OH, (C$_1$-C$_6$)-alkylene-S (O)$_p$—R6, (C$_1$-C$_6$)-alkylene-O—S(O)$_p$—R6, —O—(CH$_2$)$_m$-phenyl, —(CH$_2$)—O—(CH$_2$)$_m$-phenyl, where always at least one of the radicals R2, R2', R3, R3', R4, R4', R5, R5' has the meaning —O—(CH$_2$)$_m$-phenyl or —(CH$_2$)—O—(CH$_2$)$_m$-phenyl;

R6 is H, OH;
n is 2, 3, 4, 5, 6;
m is 1, 2, 3, 4, 5, 6;
P is 0, 1, 2.

11. The method for the production of the compound of the formula I as claimed in claim 1 or 10, wherein
R2 is H;
R2' is OH;
R3 is —O—CH$_2$-phenyl;
R3' is H;
R4 is H;
R5 is —SO$_3$H, —SO$_3^-$NH$_4^+$;
R5' is H.

12. A method for the production of the compound of the formula I as claimed in claim 11, wherein the compound of the formula I has the structure 53

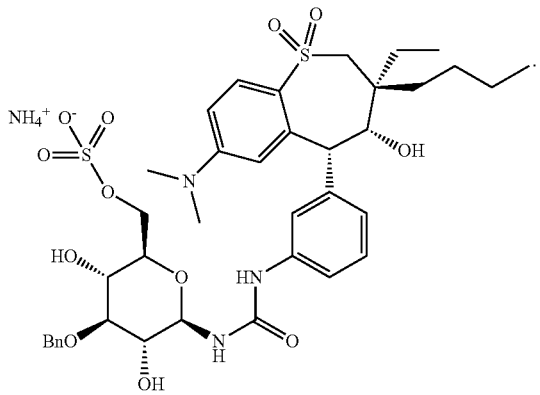

* * * * *

UNITED STATES PATENT AND TRADEMARK OFFICE
CERTIFICATE OF CORRECTION

PATENT NO. : 8,461,312 B2 Page 1 of 1
APPLICATION NO. : 12/990713
DATED : June 11, 2013
INVENTOR(S) : Guenter Billen et al.

It is certified that error appears in the above-identified patent and that said Letters Patent is hereby corrected as shown below:

On the Title Page, Item (73) should read:

(73) Assignee: Sanofi-Aventis Deutschland GmbH, Frankfurt Am Main (DE)

Signed and Sealed this
First Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,461,312 B2  
APPLICATION NO. : 12/990713  
DATED : June 11, 2013  
INVENTOR(S) : Billen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this
Eighth Day of September, 2015

Michelle K. Lee
*Director of the United States Patent and Trademark Office*